US011499169B2

(12) United States Patent
Barrangou et al.

(10) Patent No.: US 11,499,169 B2
(45) Date of Patent: Nov. 15, 2022

(54) COMPOSITIONS AND METHODS RELATED TO A TYPE-II CRISPR-CAS SYSTEM IN LACTOBACILLUS BUCHNERI

(71) Applicant: North Carolina State University, Raleigh, NC (US)

(72) Inventors: Rodolphe Barrangou, Raleigh, NC (US); Alexandra Briner Crawley, Cary, NC (US)

(73) Assignee: North Carolina State University, Raleigh, NC (US)

( * ) Notice: Subject to any disclaimer, the term of this patent is extended or adjusted under 35 U.S.C. 154(b) by 72 days.

(21) Appl. No.: 16/774,659

(22) Filed: Jan. 28, 2020

(65) Prior Publication Data

US 2020/0157576 A1    May 21, 2020

Related U.S. Application Data

(62) Division of application No. 15/032,985, filed as application No. PCT/US2014/062801 on Oct. 29, 2014, now Pat. No. 10,584,358.

(60) Provisional application No. 61/897,670, filed on Oct. 30, 2013.

(51) Int. Cl.
| | | |
|---|---|---|
| *C12N 15/90* | (2006.01) | |
| *C12N 15/74* | (2006.01) | |
| *C12N 9/22* | (2006.01) | |
| *C12N 15/11* | (2006.01) | |

(52) U.S. Cl.
CPC ............. *C12N 15/907* (2013.01); *C12N 9/22* (2013.01); *C12N 15/111* (2013.01); *C12N 15/74* (2013.01)

(58) Field of Classification Search
CPC .................... C12N 15/111; C12N 9/22
See application file for complete search history.

(56) References Cited

U.S. PATENT DOCUMENTS

| | | | |
|---|---|---|---|
| 7,919,277 B2 | 4/2011 | Russell et al. | |
| 8,361,725 B2 | 1/2013 | Russell et al. | |
| 8,697,359 B1* | 4/2014 | Zhang ............... | C12N 15/85 435/6.1 |
| 8,993,233 B2 | 3/2015 | Zhang et al. | |
| 9,023,649 B2 | 5/2015 | Mali et al. | |
| 9,260,723 B2 | 2/2016 | Mali et al. | |
| 9,701,964 B2 | 7/2017 | Clube et al. | |
| 9,951,341 B2 | 4/2018 | Horvath et al. | |
| 10,506,812 B2 | 12/2019 | Clube | |
| 2006/0199190 A1 | 9/2006 | Russell et al. | |
| 2009/0007301 A1 | 1/2009 | Wintz et al. | |
| 2010/0093617 A1 | 4/2010 | Barrangou et al. | |
| 2011/0300541 A1 | 12/2011 | Russell et al. | |
| 2013/0158245 A1 | 6/2013 | Russell et al. | |
| 2013/0288251 A1 | 10/2013 | Horvath et al. | |
| 2014/0068797 A1 | 3/2014 | Doudna et al. | |
| 2014/0113376 A1 | 4/2014 | Sorek et al. | |
| 2014/0273233 A1 | 9/2014 | Chen et al. | |
| 2014/0356867 A1 | 12/2014 | Peter et al. | |
| 2014/0356956 A1 | 12/2014 | Church et al. | |
| 2015/0050699 A1 | 2/2015 | Siksnys et al. | |
| 2015/0056628 A1 | 2/2015 | Russell et al. | |
| 2015/0064138 A1 | 3/2015 | Lu et al. | |
| 2015/0093473 A1 | 4/2015 | Barrangou et al. | |
| 2015/0098954 A1 | 4/2015 | Hyde et al. | |
| 2015/0132263 A1 | 5/2015 | Liu et al. | |
| 2015/0291961 A1 | 10/2015 | Siksnys et al. | |
| 2015/0315576 A1 | 11/2015 | Caliando et al. | |
| 2015/0353901 A1 | 12/2015 | Liu et al. | |
| 2016/0017366 A1 | 1/2016 | Chen et al. | |
| 2016/0024510 A1 | 1/2016 | Bikard et al. | |
| 2016/0186152 A1 | 6/2016 | Brouns et al. | |
| 2016/0186213 A1 | 6/2016 | Zhang et al. | |
| 2016/0345578 A1 | 12/2016 | Barrangou et al. | |
| 2017/0002339 A1 | 1/2017 | Barrangou et al. | |
| 2017/0028083 A1 | 2/2017 | Beisel et al. | |
| 2017/0073663 A1 | 3/2017 | Wang et al. | |
| 2017/0196225 A1 | 7/2017 | Clube et al. | |
| 2017/0246221 A1 | 8/2017 | Clube et al. | |
| 2017/0275648 A1 | 9/2017 | Barrangou et al. | |
| 2018/0064114 A1 | 3/2018 | Clube | |
| 2018/0064115 A1 | 3/2018 | Clube et al. | |
| 2018/0070594 A1 | 3/2018 | Clube et al. | |
| 2018/0084785 A1 | 3/2018 | Clube | |
| 2018/0084786 A1 | 3/2018 | Clube | |

(Continued)

FOREIGN PATENT DOCUMENTS

| | | |
|---|---|---|
| EP | 286267 A1 | 4/2015 |
| EP | 2860267 | 4/2015 |

(Continued)

OTHER PUBLICATIONS

Jinek et al. (2012) A Programmable Dual-RNA-Guided DNA Endonuclease in Adaptive Bacterial Immunity, Science, vol. 337, pp. 815-821.*

Barrangou et al. (2011) "CRISPR: New horizons in phage resistance and strain identification", Annu. Rev. Food Sci. Technol., vol. 3, pp. 143-162.*

Grissa et al. (2007) The CRISPRdb database and tools to display CRISPRs and to generate dictionaries of spacers and repeats, BMC Bioinform., vol. 8, No. 172, pp. 1-10.*

Liu et al. (2011) Complete Genome Sequence of Lactobacillus buchneri NRRL B-30929, a Novel Strain from a Commercial Ethanol Plant, J. Bacteriol., vol. 193, No. 15, pp. 4019-4020.*

(Continued)

*Primary Examiner* — Suzanne M Noakes
(74) *Attorney, Agent, or Firm* — Myers Bigel, P.A.

(57) ABSTRACT

The present invention is directed to methods and compositions for typing of *Lactobacillus buchneri* bacterial strains, detecting the presence of a *L. buchneri* in a sample, identifying a strain of *L. buchneri* having resistance to an invasive foreign genetic element, modifying the resistance of bacteria and archeae to an invasive foreign genetic element, and introducing nicks into or cleaving double stranded DNA for genome editing.

21 Claims, 8 Drawing Sheets

Specification includes a Sequence Listing.

(56) References Cited

U.S. PATENT DOCUMENTS

| | | | |
|---|---|---|---|
| 2018/0146681 A1 | 5/2018 | Clube | |
| 2018/0155729 A1 | 6/2018 | Beisel et al. | |
| 2018/0200387 A1 | 7/2018 | Porteus | |
| 2018/0258411 A1 | 9/2018 | Kadiyala et al. | |
| 2021/0108267 A1* | 4/2021 | Zhang | C12Q 1/6876 |

FOREIGN PATENT DOCUMENTS

| | | |
|---|---|---|
| WO | 2006/113709 | 10/2006 |
| WO | WO 2010/054154 | 5/2010 |
| WO | WO 2010/075424 | 7/2010 |
| WO | WO 2013/098244 | 7/2013 |
| WO | 2013/141680 | 9/2013 |
| WO | WO 2013/176772 | 11/2013 |
| WO | WO 2013/188522 | 12/2013 |
| WO | WO 2013/188638 | 12/2013 |
| WO | WO 2014/022702 | 2/2014 |
| WO | WO 2014/065596 | 5/2014 |
| WO | WO 2014/071235 | 5/2014 |
| WO | WO 2014/110006 | 7/2014 |
| WO | WO 2014/113493 | 7/2014 |
| WO | WO 2014/124226 | 8/2014 |
| WO | WO 2014/144155 | 9/2014 |
| WO | WO 2014/144592 | 9/2014 |
| WO | WO 2014/150624 | 9/2014 |
| WO | WO 2014/186686 | 11/2014 |
| WO | 2014/204727 | 12/2014 |
| WO | WO 2014/191128 | 12/2014 |
| WO | WO 2014/191518 | 12/2014 |
| WO | WO 2014/201015 | 12/2014 |
| WO | WO 2014/204727 | 12/2014 |
| WO | WO 2015/021353 | 2/2015 |
| WO | WO 2015/026886 | 2/2015 |
| WO | WO 2015/034872 | 3/2015 |
| WO | WO 2015/035139 | 3/2015 |
| WO | WO 2015/040402 | 3/2015 |
| WO | WO 2015/053995 | 4/2015 |
| WO | WO 2015/070193 | 5/2015 |
| WO | WO 2015/077290 | 5/2015 |
| WO | 2015/089486 | 6/2015 |
| WO | WO 2015/089277 | 6/2015 |
| WO | WO 2015/089406 | 6/2015 |
| WO | 2015112896 A2 | 7/2015 |
| WO | WO 2015/116686 | 8/2015 |
| WO | WO 2015/119941 | 8/2015 |
| WO | WO 2015/139139 | 9/2015 |
| WO | WO 2015/148680 | 10/2015 |
| WO | WO 2015/153791 | 10/2015 |
| WO | WO 2015/153889 | 10/2015 |
| WO | WO 2015/153940 | 10/2015 |
| WO | WO 2015/155686 | 10/2015 |
| WO | WO 2015/159086 | 10/2015 |
| WO | WO 2015/159087 | 10/2015 |
| WO | WO 2015/160683 | 10/2015 |
| WO | WO 2015/189693 | 12/2015 |
| WO | WO 2015/200555 | 12/2015 |
| WO | WO 2016/084088 | 6/2016 |
| WO | WO 2016/177682 | 11/2016 |
| WO | 2017027423 A1 | 2/2017 |
| WO | 2017/066497 | 4/2017 |
| WO | 2017/147507 | 8/2017 |

OTHER PUBLICATIONS

Heinl et al. (2012) Insights into the completely annotated genome of Lactobacillus buchneri CD034, a strain isolated from stable grass silage, J. Biotechnol.,, vol. 161, pp. 153-166.*
Gutierrez et al. "Predicting CRISPR-Cas9 activity in *E. coli*" bioRxviv, https://doi.org/10.1101/308148, pp. 1-22 2018.
Hochstrassera et al. "CasA mediates Cas3-catalyzed target degradation during CRISPR RNA-guided interference" PNAS, 111(18):6618-23 2014.
Nizet et al. "Bacterial sepsis and meningitis" Remington and Klein's Infectious diseases of the fetus and newborn infant, 8th Edition, pp. 217-271 2011.
Verco et al. "Cytotoxic Chromosomal Targeting by CRISPR/Cas Systems Can Reshape Bacterial Genomes and Expel or Remodel Pathogenicity Islands" PLOS Genetics, 9(4):1-13 2013.
Edgar et al. Supplemental Material "The *Escherichia coli* CRISPR System Protects from Lysogenization, Lysogens, and Prophage Induction" Journal of Bacteriology, 192(23): 6292-6294 2010.
Shinkai "Structure and Function of CRISPR-Cas System" Seibutsu Butsuri, 54(5):247-252 (2014) Abstract Only.
Extended European Search Report regarding European Application No. EP19196063, dated Jun. 26, 2020 12 pages.
Third Party Observations corresponding to European Patent Application No. 16804164.8, dated Jul. 24, 2019 60 pages.
Third Party Observations corresponding to European Patent Application No. 16812275.2, dated May 15, 2020 108 pages.
Luo et al. "The CRISPR RNA-guided surveillance complex in *Escherichia coli* accommodates extended RNA Spacers" Nucleic Acids Research, 44(15):7385-7394 2016.
Beisel CL et al. A CRISPR design for next-generation antimicrobials. Genome Biology, 2014; 15: 516, 4 pages.
Citorik RJ et al. "Sequence-specific antimicrobials using efficiently delivered RNA-guiding nucleases Supplemental Material," Nature Biotechnology. Sep. 21, 2014; 32(11): 1141-1145, DOI:10.1038/nbt.3011, 14 pages.
Cochrane Kyla et al., "Complete genome sequences and analysis of the *Fusobacterium nuleatum* subspecies *animalis* 7-1 bacteriophage PHIFunu1 and PHIFunu2", Anaerobe, 38:125-129 (2018).
Final Office Action, U.S. Appl. No. 15/113,656, dated Jul. 30, 2015, 8 pages.
International Search Report and Written Opinion for PCT/US2015/047136 dated Nov. 26, 2015, 10 pages.
Karvelis, Tautvydas et al.,"Programmable DNA cleavage in vitro by Cas9," Biochem. Soc. Trans. 2013, vol. 41, part 6, pp. 1401-1406.
Marcotte, H. et al. "Proteomes—Lactobacillus gasseri DSM 14869", NCBI Reference Sequence CP006803, (2013) URL: https://www.uniprot.org/proteomes/US000217220, retrieved Jul. 20, 2018.
Nale Janet Y. et al., "Diverse temperate bacteriophage carriage in Clostridium difficile 027 strains", PLoS One, 7(5) 1-9 (2012).
Ramakrishna Suresh et al. "Gene distruption by cell-penetrating peptide-mediated delivery of Cas9 protein and guide RNA", Genome Research, 24:1020-1027 (2014).
Uchiyama Jumpei et al., "Characterization of Helicobacter pylori bacteriophage KHP30", Applied and environmental microbiology, 79(10);3176-3184 (2013).
Written Opinion of the International Search Report regarding International Application No. PCT/US2016/067657, dated Mar. 6, 2017, 9 pages.
International Search Report and Written Opinion, PCT/US2018/034322, dated Sep. 13, 2018, 7 pages.
Novagen "pCDF-1b Vector" Sep. 10, 2003, Retrieved from the Internet on Sep. 1, 2015, at http://www.helmholtz-muenchen.de/fieadmin/PEPF/pCDF_vectors/pCDF-1b_map.pdf, 2 pages.
Final Office Action, U.S. Appl. No. 16/302,655, dated Nov. 2, 2018, 12 pp.
Final Office Action, U.S. Appl. No. 16/153,052, dated Dec. 26, 2018, 14 pages.
Final Office Action, U.S. Appl. No. 15/507,176, dated Jan. 16, 2019, 19 pages.
Claesson MJ et al. NCBI reference sequence NC_007929, direct submission Dec. 16, 2005, p. 1 (2005).
Milani C et al. Genomic encyclopedia of type strains of the genus *Bifidobacterium*. Applied and Environmental Microbiology. Oct. 2014; 80(20): 6290-6302.
Database GenBank [online]. NBI, U.S. National Library of Medicine. Aug. 5, 2014. "CRISPER-associated protein, Can1 family [Bifidobacterium bombi DSM 19703.]" XP002785852, retrieved from NCBI accession No. GenBank: KFF31259. Database accession No. KFF31259. 1 page.
Cong et al. Supplementary Materials for "Multiplex Genome Engineering Using CRISPR/Cas Systems" Science, 339(6121):819-823 (2013).
Barrsngou R. "CRISPR-Cas systems and RNA-guided interference", *Wiley interdisciplinary reviews, RNA* (2013) 4: pp. 267-278.

(56) References Cited

OTHER PUBLICATIONS

Barrangou R., et al. "CRISPR-Cas systems: prokaryotes upgrade to adaptive immunity", *Mol Cell* (2014) 54(2): pp. 234-244.
Barrangou R. "Diversity of CRISPR-Cas immune systems and molecular machines", *Genome Biology* (2015) 16:247, 11 pages.
Bhaya et al. "CRISPR-Cas Systems in Bacteria and Archaea: Versatile Small RNAs for Adaptive Defense and Regulation", *Annu. Rev. Genet.* (2011) 45: pp. 273-297.
Bikard D. et al. "Programmable repression and activation of bacterial gene expression using an engineered CRISPR-Cas system" *Nucleic Acids Res* (2013) 41(15): pp. 7429-7437.
Bikard D., et al. "CRISPR interference can prevent natural transformation and virulence acquisition during in vivo bacterial infection", *Cell Host & Microbe* (2012), 10 pages.
Bikard D., et al. "Exploiting CRISPR-Cas nucleases to produce sequence-specific antimicrobial", *Nature Biotechnology* 2014, 6 pages.
Briner et al. "Guide RNA Functional Modules Direct Cas9 Activity and Orthogonality", *Molecular Cell*. (2014) 56(2): pp. 333-339.
Brouns SJJ, et al. "Small CRISPR RNAs guide antiviral defense in prokaryotes", *Science* (2008) 321:5891, pp. 960-964.
Carte et al. "The three major types of CRISPR-Cas systems function independently in CRISPR RNA biogenesis in *Streptococcus thermophilus*", *Molecular Microbiology*, 93(1), pp. 98-112 (2014).
Chylinski et al. "Classification and evolution of type II CRISPR-Cas Systems", *Nucleic Acids Research*, (2014) 15 pages.
Citorik R., et al. "Sequence-specific antimicrobials using efficiently delivered RNA-guided nucleases", *Nature Biotechnology* 2014, 7 pages.
Darman E, Leach DF "Bacterial Genome Instability", *Microbiol. Mol. Biol. Rev.* (2014) vol. 78, pp. 1-39.
Doench et al. "Rational design of highly active sgRNAs for CRISPR-Cas9-mediated gene inactivation", *Nature Biotechnology*, 32:12 (2014) 8 pages.
Dupuis ME et al., "CRISPR-Cas and restriction modification systems are compatible and increase phage resistance", *Nat Commun.*, vol. 4, p. 2087 (2013).
Edgar R., et al. "The *Escherichia coli* CRISPR System Protects from Lysogenization, Lysogens, and Prophage Induction", *Journal of Bacteriology* (2010), vol. 192, No. 23, pp. 6202-6294.
Fonfara, I. et al. "Phylogeny of Cas9 determines functional exchangeability of dual-RNA and Cas9 among orthologous type II CRISPR-Cas systems", *Nucleic Acids Res* (2013) 14 pages.
Fu et al. "Improving CRISPR-Cas nuclease specificity using truncated guide RNAs", *Nature Biotechnology*, 32:3 (2013) 9 pages.
Gilbert et al. "Genome-Scale CRISPR-Mediated Control of Gene Repression and Activation", *Cell*, 159 (2014) pp. 647-661.
Gilbert L. A. et al. "CRISPR-Mediatad Modular RNA-Guided Regulation of Transcription in Eukaryotes", *Cell 154*, (2013) pp. 442-451.
Gomaa AA, et al. "Programmable Removal of Bacterial Strains by Use of Genome-Targeting CRISPR-Cas Systems", *mBio* (2014), 5(1):000928-13.
Haurwitz et al. "Sequence- and Structure-Specific RNA Processing by a CRISPR Endonuclease", *Science* (2010) 329: pp. 1355-1358.
Horvath and Barrangou "CRISPR/Cas, the immune System of Bacteria and Archaea", *Science* (2010) 327, pp. 167-170.
Hsu et al. "DNA targeting specificity of RNA-guided Cas9 nucleases", *Nature Biotechnology*, 31:9 (2013) pp. 827-834.
Jiang, W. et al. "Dealing with the Evolutionary Downside of CRISPR Immunity: Bacteria and Beneficial Plasmids", *PLOS Genetics* (2013) vol. 9 issue 9, 13 pages.
Jinek M. et al.,"Structures of Cas9 endonucleases reveal RNA-mediated conformational activation", *Science* (2014) vol. 343, 6176, 28 pages.
Kobayashi K, et al. "Essential *Bacillus subtilis* genes", *Proc. Natl. Acad. Sci. U.S.A.* (2003) vol. 100, pp. 4678-4683.
Labrie SJ et al. "Bacteriophage resistance mechanisms" *Nat. Rev. Microbiol* (2010) vol. 8, pp. 317-327.

Luo, M. et al., "Repurposing endogenous type I CRISPR-Cas systems for programmable gene repression", *Nucleic Acid Research* (2014) 8 pages.
Magadan et al. "Cleavage of Phage DNA by the *Streptococcus thermophilus* CRISPR3-Cas System", *PLoS One* (2012) 7:e40913. 8 pages.
Mahillon J. et al. "Insertion sequences", *Microbiol Mol Biol Rev* (1998) vol. 62(3): pp. 725-774.
Makarova and Koonin "Annotation and Classification of CRISPR-Cas Systems", *Methods Mol Biol.* (2015), 1311: pp. 47-75.
Makarova et al. "An updated evolutionary classification of CRISPR-Cas systems", *Nat. Microbiol.* 13:722-736 (2015), 15 pages.
Makarova et al. "Unification of Cas protein families and a simple scenario for the origin and evolution of CRISPRCas systems", *Biol Direct*, (2011) vol. 6:38, 27 pages.
Marraffini and Sontheimer "CRISPR Interference Limits Honzontal Gene Transfer in Staphylococci by Targeting DNA", *Science* (2005) vol. 322: pp. 1843-1845.
Nishimasu, H., et al. "Crystal Structure of Cas9 in Complex with Guide RNA and Target DNA", *Cell* (2014) vol. 156, pp. 935-949.
Notification of International Preliminary Report on Patentability corresponding to International Application No. PCT/IB2015/052515; dated Oct. 12 2016, 7 pages.
Notification and Transmittal of International Search Report and Written Opinion of the International Searching Authority for International Application No. PCT/IB2015/052515; dated Oct. 10, 2015; 12 pages.
Notification of Transmittal of the International Search Report and the Written Opinion of the International Searching Authority, or the Declaration, PCT/US2016/034812, dated Sep. 15, 2016, 9 pages.
Oh JH and van Pijkeren JP "CRISPR-Cas9-assisted recombineering in *Lactobacillus reuteri*", *Nucleic Acids Res* (2014) vol. 10.1093/nar/gku623.
Qi, L. S. et al. "Repurposing CRISPR as an RNA-Guided Platform for Sequence-Specific Control of Gene Expression", *Cell* 152, 1173-1183 (2013), 11 pages.
Sander JD, and Joung JK. "CRISPR-Cas systems for editing, regulating and targeting genomes", *Nat. Biotechnol.* (2014) vol. 32, pp. 347-355.
Seed Kimberley D. et al., "A bacteriophage encodes its own CRISPR/Cas adaptive response to evade host innate immunity", *Nature*, 494:7438, pp. 489-491 (2013).
Selle K, Barrangou R. "Harnessing, CRISPR-Cas systems for bacterial genome editing", *Cell Press: Trends Microbiol.* (2015) vol. 21(4): pp. 225-232.
Selle, K. et al. "CRISPR-based screening of genomic island excision events in bacteria", *Proc Natl Acad Sci USA*, (2015); 112(26): pp. 8076-8081.
Selle K. et al., "CRISPR-Based Technologies and the Future of Food Science", *Journal of Food Science* (2015) vol. 80, 6 pages.
Semenova et al. "Interference by clustered regularly interspaced short palindromic repeat (CRISPR) RNA is governed by a seed sequence", PNAS, 108:25 (2011) 6 pages.
Sinkuna, T. et al. "In vitro reconstitution of Cascade-mediated CRISPR immunity in *Streptococcus thermophilus*", *The EMBO Journal* (2013) vol. 32, pp. 385-394.
Stern, A. et al., "Self-targeting by CRISPR: gene regulation or autoimmunity", *Cell Press: Trends in Genetics*, (2010) vol. 26, No. 8, 6 pages.
Sternberg et al. "DNA interrogation by the CRISPR RNA-guided endonuclease Cas9", *Nature*, vol. 507, (2014) 17 pages.
Terns and Terns "CRISPR-based adaptive immune systems", *Curr. Opin. Microbiol.* (2011) vol. 14: pp. 321-327.
Vercoe RB, et al. "Cytotoxic chromosomal targeting by CRISPR/Cas systems can reshape bacterial genomes and expel or remodel pathogenicity islands", *PLoS Genet* (2013) vol. 9(4):e1003454.
Westra et al. "The CRISPRs, They Are A-Changin': How Prokaryotes Generate Adaptive Immunity", *Annu. Rev. Genet.* (2012) vol. 46: pp. 311-339.
Wiedenheft et al. "RNA-guided complex from a bacterial immune system enhances target recognition through seed sequence interactions", *PNAS*, 108:36 (2011) 7 pages.

(56) References Cited

OTHER PUBLICATIONS

Written Opinion and International Search Report corresponding to International Application No. PCT/US2016/037493, dated Sep. 15, 2016, 8 pages.
Briner et al. "Lactobacillus Buchneri genotyping on the basis of clustered regularly interspaced short palindromic repeat (CRISPR) locus diversity," *Appl Environ Microbiaol*. Nov. 22, 2013, vol. 80, No. 3, 9 pages.
Cong et al. "Multiplex genome engineering using CRISPR/Cas systems," *Science*, Jan. 3, 2013, vol. 339, No. 6121, 32 pages.
Estvelt et al. "Orthogonal Cas9 proteins for RNA-guided gene regulation and editing," *Nat Methods*, Sep. 29, 2013, vol. 10, No. 11, 42 pages.
International Preliminary Report on Patentability corresponding to International Application No. PCT/US2014/062801 (13 pages) (dated May 3, 2016).
International Search Report corresponding to International Application No. PCT/US2014/062801 (4 pages) (dated Feb. 18, 2015).
Liu et al. "Complete genome sequence of Lactobacillus buchneri NRRL B-30929, a novel strain from a commercial ethanol plant," *J. Bacteriol*. May 27, 2011, vol. 193, No. 15, 2 pages.
Barrangou and Horvath, "CRISPR: New Horizons in Phage Resistance and Strain Identification", 2012. *Annu. Rev. Food Sci. Technol*, 3:143-162.
Barrangou et al. "CRISPR Provides Acquired Resistance Against Viruses in Prokaryotes", 2007, *Science*. 315:1709-1712.
Chylinski et al. "The tracrRNA and Cas9 famillities of type II CRISPRCas immunity systems", 2013. *RNA Biol*. 10:726-737.
Crooks et al. "WebLogo: A Sequence Logo Generator", 2004, *Genome Res*. 14:1188-1190.
Deltcheva et al. "CRISPR RNA maturation by trans-encoded small RNA and host factor RNase III", 2011. *Nature* 471:602-607.
Deveau et al. "Phage Response to CRISPR-Encoded Resistance in *Streptococcus thermophilus*", 2008. *J. Bacteriol*. 190:1390-1400.
Dimarzio et al. "Antibiotic Resistance in *Salmonella enterica* Serovar Typhimurium Associates with CRISPR Sequence Type", 2013. *Antimicrob Agents Chemother* 57(9): 4282-4289.
Garneau et al."The CRISPR/Cas bacterial immune system cleaves bacteriophage and plasmid DNA", 2010. *Nature*. 468:67-71.
Gaslunas et al. "Cas9-crRNA ribonucleoprotein complex mediates specific DNA cleavage for adaptive immunity in bacteria", 2012. *Proc. Natl. Acad. Sci*. 109:E2579-E2586.
Grissa et al. "The CRISPRdb database and tools to display CRISPRs and to generate dictionaries of spcers and repeats", 2007. *BMC Bioinformatics*. 8:172.
Heini et al. "Insights into the completely annotated genome of Lactobacillus buchneri CD034, as strain isolated from stable grass silage", 2012. J. *Bacteriol*. 161:153-166.
Horvath et al. "Diversity, Activity, and Evolution of CRISPR Loci in *Streptococcus thermophilus*", 2008. *J. Bacteriol*. 190: 1401-1412.
Horvath et al. "Comparative analysis of CRISPR loci in lactic acid bacteria Genomes", 2009. *Int. J. Food Microbio*. 131:62-70.
Jiang et al. "RNA-guided editing of bacterial genomes using CRISPR-Cas system", 2013. *Nat. Biotechnol*. 31:233-239.
Jinek et al. "Bacterial Immunity A Programmable Dual-RNA-Guided DNA Endonuclease in Adaptive", 2012. *Science*. 337:816-821.
Karvelis et al. "crRNA and tracrRNA guide Cas9-mediated DNA interference in *Streptococcus thermophilus*", *RNA Biol*. 2013. 10:841-851.
Liu et al. "Subtyping *Salmonella enterica* Serovar Enteritidis Isolates from Different Source by Using Sequence Typing Bases on Virulence Genes and Clustered Regularly Interspaced Short Palindromic Repeats (CRISPRs)", 2011. *Appl. Environ. Microbiol*. 77:4520-4526.
Liu et al. "Novel Virulence Gene and Clustered Regularly Interspaced Short Palindromic Repeat (CRISPR) Multilocus Sequence Typing Scheme for Subtyping of the Major Serovars of *Salmonella enterica* subsp. *Enteric*", 2011. *Appl. Environ. Microbiol*. 77:1946-1956.

Makarova et al. "Evolution and classification of the CRISPR-Cas systems", 2011. *Nature Rev. Microbiol*. 9:467-477.
Mali, Prashant et al. "RNA-Guided Human Genome Engineering via Cas9", 2013. *Science*. 339:823-826.
Mojica et al. "Short motif sequences determine the targets of the prokaryotic CRISPR defence system", 2009. *Microbiology*. 155:733-740.
Paez-Espino et al. "Strong bias in the bacterial CRISPR elements that confer immunity to phage", 2013. *Nat. Commun*. 4:1430.
Sapranauskas et al. "The *Streptococcus thermophilus* CRISPR/Cas system provided immunity in *Escherichia coli*", 2011. *Nucleic Acid Res*. 39:9275-9282.
Shariat, Nikki et al. "Subtyping of *Salmonella enterica* Serovar Newport Outbreak Isolates by CRISPR-MVLST and Determination of the Relationship between CRISPR-MVLST and PFGE Results", 2013. *J. Clin. Microbiol*. 51:2328-2336.
Shariat, Nikki et al. "The combination of CRISPR-MVLST and PFGE provides increased discriminatory power for differentiating human clinical isolates of *Salmonella enterica* subsp. *enterica* serovar Enteritidis", 2013. *Food Microbiol*. 34:164-173.
Weinberger, Ariel et al. "Persisting Viral Sequences Shape Microbial CRISPR based Immunity", 2012. *PLoS Comput Biol*. 8:e1002475.
Yin, Shuang et al. "The Evolutionary Divergence of Shiga Toxin-Producint *Escherichia coli* Is Reflected in Clustered Regularly Interspaced Short Palindromic Repeat (CRISPR) Spacer Composition", 2013. *Appl. Environ. Microbiol*. 79:5710-5720.
Grissa I et al. The CRISPRdb database and tools to display CRISPRs and to generate dictionaries of spacers and repeats. BMC Bioinformatics. 2007; 8(172): pp. 1-10.
Liu S et al. Complete genome sequence of Lactobacillus buchneri NRRL B-30929; a novel strain from a commercial ethanol plant. Journal of Bacteriology. Aug. 2011; 194(15): 4019-4020.
Liu S et al. NCBI (2011) CRISPR-associated protein, Csn1 family [Lactobacillus buchneri], pp. 1-3.
Rath D et al. The CRISPR-Cas immune system: Biology, mechanisms and applications. Biochimie. 2015;117:119-128.
Spath K et al. Lactobacillus plantarum and Lactobacillus buchneri as expression systems: Evaluation of different origins of replication for the design of suitable shuttle vectors. Mol. Biotechnol. 2012; 52: 40-48.
Anderson et al. "Lactobacillus gasseri CRISPR-Cas9 characterization In Vitro reveals a flexible mode of protospacer-adjacent motif recognition" PLOS ONE, 13(2) 14 pages 2018.
Gasiunas et al. "Molecular mechanisms of CRISPR-mediated microbial immunity" Cellular and Molecular Life Sciences, 71:449-465 (2014).
GenBank Accession No. FN692037.1, "Lactobacillus crispatus ST1 complete genome, strain ST1" Feb. 27, 2015.
Hidalgo-Cantabrana et al. "Genome editing using the endogenous type I CRISPR-Cas system in Lactobacillus crispatus" PNAS, 116)32):15774-15763 (2019).
International Preliminary Report on Patentability Notification, PCT/US2018/034322, dated Dec. 5, 2019, 7 pages.
International Search Report and Written Opinion corresponding to PCT/US2019/52861, dated Feb. 12, 2020, 18 pages.
International Search Report and Written Opinion corresponding to PCT/US2019/52864, dated Dec. 17, 2019, 15 pages.
International Search Report and Written Opinion corresponding to PCT/US2019/52878, dated Dec. 27, 2019, 14 pages.
International Search Report and Written Opinion corresponding to PCT/US2019/52883, dated Dec. 23, 2019, 9 pages.
Ojala et al. "Comparative genomics of Lactobacillus crispatus suggests novel mechanisms for the competitive exclusion of Garnerella vaginalis" BNC Genomics, 15:1070 (2014).
Sanozky-Dawes et al. "Occurrence and activity of a type II CRISPR-Cas system in Lactobacillus gasseri" Microbiology, 161:1752-1761 2015.
Westra et al. "CRISPR Immunity Relies on the Consecutive Binding and Degradation of Negatively Supercoiled Invader DNA by Cascade and Cas3" Molecular Cell, 46:595-605 (2012).

(56) References Cited

OTHER PUBLICATIONS

Yosef et al. "High-temperature protein G is essential for activity of the *Escherichia coli* clustered regularly interspaced short palindromic repeats (CRISPR)/Cas system" Proc Natl Acad Sci, 108(50):20136-20141 (2011).

Chauthaiwale, V. M. et al. "Bacteriophage Lamda as a Cloning Vector" Microbiological Reviews, 56(4):1577-591 (1992).

Dang, Y. et al. "Optimizing sgRNA structure to improve CRISPR-Cas9 knockout efficiency" Genome Biology, 16(280):11-10 (2015).

Edgar, R. et al. "Reversing Bacterial Resistance to Antibiotics by Phage-Mediated Delivery of Dominant Sensitive Genes" Applied and Environmental Microbiology, 78(3):1744-751 (2011).

Extended European Search Report corresponding to European Patent Application No. 18806333.3 (8 pages) (dated Feb. 9, 2021).

Third Party Observation filed in European Patent Application No. 16804164.8 on Feb. 19, 2021, 15 pages.

Third Party Observation filed in European Patent Application No. 16812275.2 on Feb. 19, 2021, 38 pages.

Yosef, I. et al. "Temperate and lytic bacteriophages programmed to sensitize and kill antibiotic-resistant bacteria" PNAS, 112(23):17267-7272 (2015).

Sashital et al. "Mechanism of foreign DNA selection in a bacterial adaptive immune system" Mol Cell., 46(5):6061-615 2012.

Third Party Observations corresponding to U.S. Appl. No. 15/735,028, dated Aug. 30, 2019 17 pages.

Boudry et al. "Function of CRISPR-Cas System of the Human Pathogen Clostridium difficile" mBio, 6(5):1-15 2015.

Ramakrishna et al. "Gene disruption by cell-penetrating peptide-mediated delivery of Cas9 protein and guide RNA", Genome Research, 24:1020-1027 (2014).

Lecuit, et al., "Internalin of Listeria monocytogenes with an Intact Leucine-Rich Repeat Region Is Sufficient To Promote Internalization", Infection and Immunity. vol. 65, No. 12, pp. 5309-5319 (1997).

Wilson, et al., Principles and Techniques of Biochemistry and Molecular Biology. 7th ed. Cambridge University Press, pp. 214-218 (2010).

\* cited by examiner

SEQUENCE LISTING

<160> NUMBER OF SEQ ID NOS: 64

<210> SEQ ID NO 1
<211> LENGTH: 1371
<212> TYPE: PRT
<213> ORGANISM: Lactobacillus buchneri

<400> SEQUENCE: 1

Met Lys Val Asn Asn Tyr His Ile Gly Leu Asp Ile Gly Thr Ser Ser
1               5                   10                  15

Ile Gly Trp Val Ala Ile Gly Glu Asp Gly Lys Pro Leu Arg Ile Lys
            20                  25                  30

Gly Lys Thr Ala Ile Gly Ala Arg Leu Phe Gln Glu Gly Asn Pro Ala
        35                  40                  45

Ala Asp Arg Arg Met Phe Arg Thr Thr Arg Arg Leu Ser Arg Arg
    50                  55                  60

Lys Trp Arg Leu Lys Leu Leu Glu Glu Ile Phe Asp Pro Tyr Ile Thr
65                  70                  75                  80

Pro Val Asp Ser Thr Phe Phe Ala Arg Leu Lys Gln Ser Asn Leu Ser
                85                  90                  95

Pro Lys Asp Ser Arg Lys Glu Phe Lys Gly Ser Met Leu Phe Pro Asp
            100                 105                 110

Leu Thr Asp Met Gln Tyr His Lys Asp Tyr Pro Thr Ile Tyr His Leu
        115                 120                 125

Arg His Ala Leu Met Thr Gln Asp Glu Lys Phe Asp Ile Arg Met Val
    130                 135                 140

Tyr Leu Ala Ile His His Ile Val Lys Tyr Arg Gly Asn Phe Leu Asn

-continued

```
            145                 150                 155                 160
        Ser Thr Pro Val Asp Ser Phe Lys Ala Ser Lys Val Asn Phe Val Asp
                            165                 170                 175

Gln Phe Lys Lys Leu Asn Glu Leu Tyr Thr Ala Ile Asn Pro Glu Glu
                            180                 185                 190

Ser Phe Gln Ile Asn Leu Ala Asn Ser Glu Asp Ile Gly His Gln Phe
                            195                 200                 205

Leu Asp Pro Ser Ile Arg Lys Phe Asp Lys Lys Gln Ile Pro Lys
            210                 215                 220

Ile Val Pro Val Ser Val Asp Lys Ala Thr Asp Lys Ile Asn Gly
        225                 230                 235                 240

Lys Ile Ala Ser Glu Ile Ile Asn Ala Ile Leu Gly Tyr Lys Ser Lys
                            245                 250                 255

Leu Asp Val Val Val Gln Cys Thr Pro Val Asp Ser Lys Ser Trp Ala
                            260                 265                 270

Leu Lys Phe Asp Glu Glu Asp Ile Asp Ala Lys Leu Gln Lys Ile Leu
                            275                 280                 285

Pro Glu Met Asp Glu Asn Gln Gln Ser Ile Ile Ala Ile Leu Gln Asn
                            290                 295                 300

Leu Tyr Ser Gln Val Thr Leu Asn Gln Ile Val Pro Asn Gly Met Ser
        305                 310                 315                 320

Leu Ser Glu Ser Met Ile Glu Lys Tyr Asn Asp His His Asp His Leu
                            325                 330                 335

Lys Leu Tyr Lys Lys Ile Ile Asp Gln Leu Ala Asp Pro Lys Lys Lys
                            340                 345                 350

Ala Ala Leu Lys Lys Ala Tyr Ser Gln Tyr Val Gly Asp Asp Gly Lys
                            355                 360                 365

Val Ile Glu Gln Ala Asp Phe Trp Ser Val Lys Lys Asn Leu Asp
            370                 375                 380

Asp Ser Asp Leu Ser Lys Gln Ile Met Asp Leu Ile Asp Ala Glu Lys
        385                 390                 395                 400

Phe Met Pro Lys Gln Arg Thr Ser Gln Asn Gly Val Ile Pro His Gln
                            405                 410                 415

Leu His Gln Arg Glu Leu Asp Glu Ile Ile Glu His Gln Ser Lys Tyr
                            420                 425                 430

Tyr Pro Trp Leu Ala Glu Ile Asn Pro Asn Lys His Asp Leu His Leu
                            435                 440                 445

Ala Lys Tyr Lys Ile Glu Glu Leu Val Ala Phe Arg Val Pro Tyr Tyr
            450                 455                 460

Val Gly Pro Met Ile Thr Pro Asp Asp Gln Ala Lys Ser Ala Glu Thr
        465                 470                 475                 480

Val Phe Ser Trp Met Glu Arg Lys Gly Lys Glu Ala Gly Gln Ile Thr
                            485                 490                 495

Pro Trp Asn Phe Asp Glu Lys Val Asp Arg Asn Ala Ser Ala Asn Arg
                            500                 505                 510

Phe Ile Lys Arg Met Thr Thr Lys Asp Thr Tyr Leu Ile Gly Glu Asp
                            515                 520                 525

Val Leu Pro Asp Glu Ser Leu Tyr Glu Lys Phe Lys Val Leu Asn
            530                 535                 540

Glu Leu Asn Met Val Arg Val Asn Gly Lys Leu Leu Lys Val Ala Asp
        545                 550                 555                 560

Lys Gln Ala Ile Phe Gln Asp Leu Phe Glu Asn Tyr Lys His Ile Ser
                            565                 570                 575
```

```
Val Lys Lys Leu Gln Asn Tyr Ile Lys Ser Lys Thr Gly Leu Pro Ser
            580                 585                 590

Asp Pro Glu Ile Ser Gly Leu Ser Asp Pro Glu Tyr Phe Asn Asn Ser
        595                 600                 605

Leu Gly Thr Tyr Asn Asp Phe Lys Lys Leu Phe Gly Asn Lys Val Asp
    610                 615                 620

Glu Pro Asp Leu Gln Asp Asp Phe Glu Lys Ile Val Glu Trp Ser Thr
625                 630                 635                 640

Val Phe Glu Asp Lys Arg Ile Leu Arg Glu Lys Leu Asn Glu Ile Thr
                645                 650                 655

Trp Leu Ser Asp Gln Gln Lys Asp Val Leu Glu Ser Ser Arg Tyr Gln
            660                 665                 670

Gly Trp Gly Arg Leu Ser Lys Lys Leu Leu Thr Gly Ile Val Asn Asp
        675                 680                 685

Gln Gly Glu Arg Ile Ile Asp Glu Leu Trp Asn Thr Asn Lys Asn Phe
    690                 695                 700

Met Gln Ile Gln Ser Asp Asn Asp Phe Ala Lys Arg Ile His Glu Ala
705                 710                 715                 720

Asn Ala Asp Gln Met Lys Ala Val Asp Val Glu Asp Val Leu Ala Asp
                725                 730                 735

Ala Tyr Thr Ser Pro Gln Asn Lys Lys Ala Ile Arg Gln Val Val Lys
            740                 745                 750

Val Val Asp Asp Ile Gln Lys Ala Met Gly Gly Val Ala Pro Lys Tyr
        755                 760                 765

Ile Ser Ile Glu Phe Thr Arg Ser Glu Asp Arg Asn Pro Arg Arg Thr
    770                 775                 780

Ile Ser Arg Gln Arg Gln Leu Glu Asn Thr Leu Lys Asp Thr Ala Lys
785                 790                 795                 800

Ser Leu Ala Lys Ser Ile Asn Pro Glu Leu Leu Ser Glu Leu Asp Asn
                805                 810                 815

Ala Ala Lys Ser Lys Lys Gly Leu Thr Asp Arg Leu Tyr Leu Tyr Phe
            820                 825                 830

Thr Gln Leu Gly Lys Asp Ile Tyr Thr Gly Lys Pro Ile Asn Ile Asp
        835                 840                 845

Glu Ile Ser Thr Tyr Asp Ile Asp His Ile Leu Pro Gln Ala Phe Val
    850                 855                 860

Lys Asp Asp Ser Leu Asn Asn Arg Val Leu Val Ser Lys Ala Ile Asn
865                 870                 875                 880

Asn Gly Lys Ser Asp Asn Val Pro Val Gln Leu Phe Gly Ala Lys Met
                885                 890                 895

Gly His Phe Trp Lys Gln Leu Ala Glu Ala Gly Leu Ile Ser Lys Arg
            900                 905                 910

Lys Leu Lys Asn Leu Gln Thr Asp Pro Asp Thr Ile Ser Lys Tyr Ala
        915                 920                 925

Met His Gly Phe Ile Arg Arg Gln Leu Val Glu Thr Ser Gln Val Ile
    930                 935                 940

Lys Leu Val Ala Asn Ile Leu Gly Asp Lys Tyr Arg Asn Asp Asn Thr
945                 950                 955                 960

Lys Ile Ile Glu Ile Thr Ala Arg Met Asn His Gln Met Arg Asp Glu
                965                 970                 975

Phe Gly Phe Ile Lys Asn Arg Glu Ile Asn Asp Tyr His His Ala Phe
            980                 985                 990
```

```
Asp Ala Tyr Leu Thr Ala Phe Leu Gly Arg Tyr Leu Tyr His Arg Tyr
        995                 1000                1005

Ile Lys Leu Arg Pro Tyr Phe Val Tyr Gly Asp Phe Lys Lys Phe
1010                1015                1020

Lys Glu Asp Lys Val Thr Met Arg Asn Phe Asn Phe Leu His Asp
1025                1030                1035

Leu Thr Asp Asp Thr Gln Glu Lys Ile Ala Asp Ala Glu Thr Gly
1040                1045                1050

Glu Val Ile Trp Asp Arg Glu Asn Ser Ile Gln Gln Leu Lys Asp
1055                1060                1065

Val Tyr His Tyr Lys Phe Met Leu Ile Ser His Glu Val Tyr Thr
1070                1075                1080

Leu Arg Gly Ala Met Phe Asn Gln Thr Val Tyr Pro Ala Ser Asp
1085                1090                1095

Ala Gly Lys Arg Lys Leu Ile Pro Ile Lys Ala Asp Arg Pro Ile
1100                1105                1110

Asn Val Tyr Gly Gly Tyr Ser Gly Ser Ala Asp Ala Tyr Met Ala
1115                1120                1125

Ile Val Arg Ile His Asn Lys Lys Gly Asp Lys Tyr Arg Val Val
1130                1135                1140

Gly Val Pro Met Arg Ala Arg Asp Arg Leu Asp Ala Ala Lys Lys
1145                1150                1155

Val Ser Asp Ala Asp Cys Asp Arg Ala Leu Lys Asp Val Leu Thr
1160                1165                1170

Pro Gln Leu Thr Lys Thr Lys Lys Ser Arg Lys Thr Gly Glu Ile
1175                1180                1185

Thr Gln Val Val Glu Asp Phe Glu Ile Val Leu Gly Lys Val Met
1190                1195                1200

Tyr Arg Gln Leu Met Ile Asp Gly Asp Lys Lys Phe Met Leu Gly
1205                1210                1215

Ser Ser Thr Tyr Gln Tyr Asn Ala Lys Gln Leu Val Leu Ser Asp
1220                1225                1230

Gln Ser Val Lys Thr Leu Ala Ser Lys Gly Arg Leu Asp Pro Leu
1235                1240                1245

Gln Glu Ser Met Asp Tyr Asn Asn Val Tyr Thr Glu Ile Leu Asp
1250                1255                1260

Lys Val Asn Gln Tyr Phe Ser Leu Tyr Asp Met Asn Lys Phe Arg
1265                1270                1275

His Lys Leu Asn Leu Gly Phe Ser Lys Phe Ile Ser Phe Pro Asn
1280                1285                1290

His Asn Val Phe Asp Gly Asn Thr Lys Ala Ser Ser Gly Lys Arg
1295                1300                1305

Glu Ile Leu Glu Glu Val Leu Asn Gly Leu His Ala Asn Pro Thr
1310                1315                1320

Phe Gly Asn Leu Lys Asp Ile Gly Ile Thr Thr Pro Phe Gly Gln
1325                1330                1335

Leu Gln Gln Pro Asn Gly Ile Leu Leu Ser Asp Glu Ala Lys Ile
1340                1345                1350

Arg Tyr Gln Ser Pro Thr Gly Leu Phe Glu Arg Thr Val Ser Leu
1355                1360                1365

Lys Asp Leu
1370
```

```
<210> SEQ ID NO 2
<211> LENGTH: 36
<212> TYPE: DNA
<213> ORGANISM: Lactobacillus buchneri

<400> SEQUENCE: 2
gttttagaag gatgttaaat cataaggtt aaaccc                                    36

<210> SEQ ID NO 3
<211> LENGTH: 20
<212> TYPE: DNA
<213> ORGANISM: Lactobacillus buchneri

<400> SEQUENCE: 3
auuuaacauc cuguguuaaa                                                     20

<210> SEQ ID NO 4
<211> LENGTH: 18
<212> TYPE: DNA
<213> ORGANISM: Artificial
<220> FEATURE:
<223> OTHER INFORMATION: PCR primer

<400> SEQUENCE: 4
gctttagtag ttcaaaac                                                       18

<210> SEQ ID NO 5
<211> LENGTH: 22
<212> TYPE: DNA
<213> ORGANISM: Artificial
<220> FEATURE:
<223> OTHER INFORMATION: PCR primer

<400> SEQUENCE: 5
catcattgtt ttgaactact ac                                                  22

<210> SEQ ID NO 6
<211> LENGTH: 23
<212> TYPE: DNA
<213> ORGANISM: Artificial
<220> FEATURE:
<223> OTHER INFORMATION: PCR primer

<400> SEQUENCE: 6
gggtttaacc ttattgattt aac                                                 23

<210> SEQ ID NO 7
<211> LENGTH: 22
<212> TYPE: DNA
<213> ORGANISM: Artificial
<220> FEATURE:
<223> OTHER INFORMATION: PCR primer

<400> SEQUENCE: 7
gaaggatgtt aaatcaataa gg                                                  22

<210> SEQ ID NO 8
<211> LENGTH: 18
<212> TYPE: DNA
<213> ORGANISM: Artificial
<220> FEATURE:
<223> OTHER INFORMATION: PCR primer

<400> SEQUENCE: 8
ccttcagact gacggttc                                                       18
```

```
<210> SEQ ID NO 9
<211> LENGTH: 19
<212> TYPE: DNA
<213> ORGANISM: Artificial
<220> FEATURE:
<223> OTHER INFORMATION: PCR primer

<400> SEQUENCE: 9
gtctcgatat tgggacctc                                                 19

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
ccagaatgaa tgatctgttg                                                20

<210> SEQ ID NO 11
<211> LENGTH: 17
<212> TYPE: DNA
<213> ORGANISM: Artificial
<220> FEATURE:
<223> OTHER INFORMATION: PCR primer

<400> SEQUENCE: 11
catcgacgag aactttg                                                   17

<210> SEQ ID NO 12
<211> LENGTH: 7
<212> TYPE: PRT
<213> ORGANISM: Lactobacillus buchneri

<400> SEQUENCE: 12

Ile Gly Leu Asp Ile Gly Thr
1               5

<210> SEQ ID NO 13
<211> LENGTH: 5
<212> TYPE: PRT
<213> ORGANISM: Artificial
<220> FEATURE:
<223> OTHER INFORMATION: L. buchneri conserved sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 13

His Xaa Asn Xaa Asn
1               5

<210> SEQ ID NO 14
<211> LENGTH: 6
<212> TYPE: PRT
<213> ORGANISM: Lactobacillus buchneri

<400> SEQUENCE: 14

Tyr Asp Ile Asp His Ile
1               5
```

```
<210> SEQ ID NO 15
<211> LENGTH: 5
<212> TYPE: PRT
<213> ORGANISM: Lactobacillus buchneri

<400> SEQUENCE: 15

Asn Asn Arg Val Leu
1               5

<210> SEQ ID NO 16
<211> LENGTH: 4
<212> TYPE: PRT
<213> ORGANISM: Lactobacillus buchneri

<400> SEQUENCE: 16

Ile Asn Asn Gly
1

<210> SEQ ID NO 17
<211> LENGTH: 10
<212> TYPE: DNA
<213> ORGANISM: Lactobacillus buchneri

<400> SEQUENCE: 17
aaaattcaga                                                          10

<210> SEQ ID NO 18
<211> LENGTH: 30
<212> TYPE: DNA
<213> ORGANISM: Lactobacillus buchneri

<400> SEQUENCE: 18
caacaaaaaa agcgctccgc aacggccatt                                    30

<210> SEQ ID NO 19
<211> LENGTH: 10
<212> TYPE: DNA
<213> ORGANISM: Lactobacillus buchneri

<400> SEQUENCE: 19
gcaaaacgct                                                          10

<210> SEQ ID NO 20
<211> LENGTH: 10
<212> TYPE: DNA
<213> ORGANISM: Lactobacillus buchneri

<400> SEQUENCE: 20
atgaagttca                                                          10

<210> SEQ ID NO 21
<211> LENGTH: 30
<212> TYPE: DNA
<213> ORGANISM: Lactobacillus buchneri

<400> SEQUENCE: 21
agctgtgtca aactacgttg aatcccaagg                                    30

<210> SEQ ID NO 22
<211> LENGTH: 10
<212> TYPE: DNA
<213> ORGANISM: Lactobacillus buchneri

<400> SEQUENCE: 22
```
acaaaactta                                                              10

<210> SEQ ID NO 23
<211> LENGTH: 10
<212> TYPE: DNA
<213> ORGANISM: Lactobacillus buchneri

<400> SEQUENCE: 23
ctggttttat                                                              10

<210> SEQ ID NO 24
<211> LENGTH: 30
<212> TYPE: DNA
<213> ORGANISM: Lactobacillus buchneri

<400> SEQUENCE: 24
aaacggatat tgcggcttat attaacgagc                                        30

<210> SEQ ID NO 25
<211> LENGTH: 10
<212> TYPE: DNA
<213> ORGANISM: Lactobacillus buchneri

<400> SEQUENCE: 25
tgaaatggtt                                                              10

<210> SEQ ID NO 26
<211> LENGTH: 10
<212> TYPE: DNA
<213> ORGANISM: Lactobacillus buchneri

<400> SEQUENCE: 26
ctggttttat                                                              10

<210> SEQ ID NO 27
<211> LENGTH: 30
<212> TYPE: DNA
<213> ORGANISM: Lactobacillus buchneri

<400> SEQUENCE: 27
aaacggatat tgcggcttat attaacgagc                                        30

<210> SEQ ID NO 28
<211> LENGTH: 10
<212> TYPE: DNA
<213> ORGANISM: Lactobacillus buchneri

<400> SEQUENCE: 28
tgaaatggtt                                                              10

<210> SEQ ID NO 29
<211> LENGTH: 10
<212> TYPE: DNA
<213> ORGANISM: Lactobacillus buchneri

<400> SEQUENCE: 29
agaatatcga                                                              10

<210> SEQ ID NO 30
<211> LENGTH: 30
<212> TYPE: DNA
<213> ORGANISM: Lactobacillus buchneri

```
<400> SEQUENCE: 30
caacgcagct aaagataatc gtcagaatta                                    30

<210> SEQ ID NO 31
<211> LENGTH: 10
<212> TYPE: DNA
<213> ORGANISM: Lactobacillus buchneri

<400> SEQUENCE: 31
ccagaaatta                                                          10

<210> SEQ ID NO 32
<211> LENGTH: 10
<212> TYPE: DNA
<213> ORGANISM: Lactobacillus buchneri

<400> SEQUENCE: 32
taagcttggt                                                          10

<210> SEQ ID NO 33
<211> LENGTH: 30
<212> TYPE: DNA
<213> ORGANISM: Lactobacillus buchneri

<400> SEQUENCE: 33
ggaaaaaggt ggcggccgct ttgtgcaagg                                    30

<210> SEQ ID NO 34
<211> LENGTH: 10
<212> TYPE: DNA
<213> ORGANISM: Lactobacillus buchneri

<400> SEQUENCE: 34
tcaagaaatg                                                          10

<210> SEQ ID NO 35
<211> LENGTH: 10
<212> TYPE: DNA
<213> ORGANISM: Lactobacillus buchneri

<400> SEQUENCE: 35
ttacgcttta                                                          10

<210> SEQ ID NO 36
<211> LENGTH: 30
<212> TYPE: DNA
<213> ORGANISM: Lactobacillus buchneri

<400> SEQUENCE: 36
accgagtttc gtgatctcaa aagtagctac                                    30

<210> SEQ ID NO 37
<211> LENGTH: 10
<212> TYPE: DNA
<213> ORGANISM: Lactobacillus buchneri

<400> SEQUENCE: 37
gcaaaaacta                                                          10

<210> SEQ ID NO 38
<211> LENGTH: 10
<212> TYPE: DNA
<213> ORGANISM: Lactobacillus buchneri
```

```
<400> SEQUENCE: 38
ttcttagatg                                                            10

<210> SEQ ID NO 39
<211> LENGTH: 30
<212> TYPE: DNA
<213> ORGANISM: Lactobacillus buchneri

<400> SEQUENCE: 39
ccgcttactt gccgttaaag cgggatatcg                                      30

<210> SEQ ID NO 40
<211> LENGTH: 10
<212> TYPE: DNA
<213> ORGANISM: Lactobacillus buchneri

<400> SEQUENCE: 40
ttcaaaaga                                                             10

<210> SEQ ID NO 41
<211> LENGTH: 10
<212> TYPE: DNA
<213> ORGANISM: Lactobacillus buchneri

<400> SEQUENCE: 41
aaaattcaga                                                            10

<210> SEQ ID NO 42
<211> LENGTH: 30
<212> TYPE: DNA
<213> ORGANISM: Lactobacillus buchneri

<400> SEQUENCE: 42
caacaaaaaa agcgctccgc aacggccatt                                      30

<210> SEQ ID NO 43
<211> LENGTH: 10
<212> TYPE: DNA
<213> ORGANISM: Lactobacillus buchneri

<400> SEQUENCE: 43
gcaaaacgct                                                            10

<210> SEQ ID NO 44
<211> LENGTH: 10
<212> TYPE: DNA
<213> ORGANISM: Lactobacillus buchneri

<400> SEQUENCE: 44
cattatgcta                                                            10

<210> SEQ ID NO 45
<211> LENGTH: 30
<212> TYPE: DNA
<213> ORGANISM: Lactobacillus buchneri

<400> SEQUENCE: 45
aaggttcagg tgtctcacac gctgaactag                                      30

<210> SEQ ID NO 46
<211> LENGTH: 10
<212> TYPE: DNA
```

```
<213> ORGANISM: Lactobacillus buchneri

<400> SEQUENCE: 46
acaaaattat                                                          10

<210> SEQ ID NO 47
<211> LENGTH: 10
<212> TYPE: DNA
<213> ORGANISM: Lactobacillus buchneri

<400> SEQUENCE: 47
ctttatctag                                                          10

<210> SEQ ID NO 48
<211> LENGTH: 30
<212> TYPE: DNA
<213> ORGANISM: Lactobacillus buchneri

<400> SEQUENCE: 48
gaaataagca gcctcatttg aagcaccatg                                    30

<210> SEQ ID NO 49
<211> LENGTH: 10
<212> TYPE: DNA
<213> ORGANISM: Lactobacillus buchneri

<400> SEQUENCE: 49
ccaaaaatga                                                          10

<210> SEQ ID NO 50
<211> LENGTH: 28
<212> TYPE: DNA
<213> ORGANISM: Lactobacillus buchneri

<400> SEQUENCE: 50
gtattcccca cgtacgtagg ggtgatcc                                      28

<210> SEQ ID NO 51
<211> LENGTH: 28
<212> TYPE: DNA
<213> ORGANISM: Lactobacillus buchneri

<400> SEQUENCE: 51
gtattcccca cgtgtgtagg ggtgatcc                                      28

<210> SEQ ID NO 52
<211> LENGTH: 28
<212> TYPE: DNA
<213> ORGANISM: Lactobacillus buchneri

<400> SEQUENCE: 52
gtattcccca tgtatgtggg ggtgatcc                                      28

<210> SEQ ID NO 53
<211> LENGTH: 28
<212> TYPE: DNA
<213> ORGANISM: Lactobacillus brevis

<400> SEQUENCE: 53
gtattcccca cacatgtggg ggtgatcc                                      28

<210> SEQ ID NO 54
<211> LENGTH: 28
```

```
<212> TYPE: DNA
<213> ORGANISM: Lactobacillus brevis

<400> SEQUENCE: 54
gtattcccca caggtgtggg ggtgatcc                                     28

<210> SEQ ID NO 55
<211> LENGTH: 50
<212> TYPE: DNA
<213> ORGANISM: Lactobacillus buchneri

<400> SEQUENCE: 55
cattatgcta aaggttcagg tgtctcacac gctgaactca acaaaattat             50

<210> SEQ ID NO 56
<211> LENGTH: 102
<212> TYPE: DNA
<213> ORGANISM: Lactobacillus buchneri

<400> SEQUENCE: 56
gttttagaag gatgttaaat caataaggtt aaacccaagg ttcaggtgtc tcacacgctg  60
aactcagttt tagaaggatg ttaaatcaat aaggttaaac cc                    102

<210> SEQ ID NO 57
<211> LENGTH: 90
<212> TYPE: DNA
<213> ORGANISM: Lactobacillus buchneri

<400> SEQUENCE: 57
auguuugacc uuauugauuu aacauccugu guuaaaauca agcaaagcgc uuugcgcgga  60
guuucaacuu uugacccauu auaugggcau                                  90

<210> SEQ ID NO 58
<211> LENGTH: 40
<212> TYPE: DNA
<213> ORGANISM: Lactobacillus buchneri

<400> SEQUENCE: 58
ugucucacac gcugaacuca guuuuagaag gauguuaaau                        40

<210> SEQ ID NO 59
<211> LENGTH: 50
<212> TYPE: DNA
<213> ORGANISM: Lactobacillus buchneri

<400> SEQUENCE: 59
ataattttgt tgagttcagc gtgtgagaca cctgaacctt tagcataatg             50

<210> SEQ ID NO 60
<211> LENGTH: 137
<212> TYPE: DNA
<213> ORGANISM: Lactobacillus buchneri

<400> SEQUENCE: 60
guuugaccuu auugauuuaa cauccugugu ugaaaucaag caaagcgcuu ugcgcggagu  60
uucaacuuuu gacccauuau augggcauua cauaagcgaa aggaaccauu cuucaguugg  120
agaaugguuc cuuuuuu                                                137

<210> SEQ ID NO 61
<211> LENGTH: 36
<212> TYPE: DNA
```

```
<213> ORGANISM: Artificial Sequence
<220> FEATURE:
<223> OTHER INFORMATION: target nucleic acid non-PAM strand
<220> FEATURE:
<221> NAME/KEY: misc_feature
<222> LOCATION: (5)..(6)
<223> OTHER INFORMATION: n is a, c, g, t or u

<400> SEQUENCE: 61
ttttnntgta tcctcactct ctccgacagt cacctc                               36

<210> SEQ ID NO 62
<211> LENGTH: 35
<212> TYPE: DNA
<213> ORGANISM: Artificial Sequence
<220> FEATURE:
<223> OTHER INFORMATION: target nucleic acid PAM strand
<220> FEATURE:
<221> NAME/KEY: misc_feature
<222> LOCATION: (31)..(32)
<223> OTHER INFORMATION: n is a, c, g, t or u

<400> SEQUENCE: 62
gaggtgactg tcggagagag tgaggataca nnaaa                                35

<210> SEQ ID NO 63
<211> LENGTH: 185
<212> TYPE: DNA
<213> ORGANISM: Artificial Sequence
<220> FEATURE:
<223> OTHER INFORMATION: single guide

<400> SEQUENCE: 63
gaggtgactg tcggagagag ggaggatgca guuuagaag gauguuaaau caauuguuau      60
ugauuuaaca uccuguguug aaaucaagca aagcgcuuug cgcggaguuu caacuuuuga    120
cccauuauau gggcauuaca uaagcgaaag gaaccauucu ucaguuggag aaugguuccu    180
uuuuu                                                                185

<210> SEQ ID NO 64
<211> LENGTH: 64
<212> TYPE: DNA
<213> ORGANISM: Artificial Sequence
<220> FEATURE:
<223> OTHER INFORMATION: CRISPR nucleic acid

<400> SEQUENCE: 64
gaggtgactg tcggagagag ggaggatgca guuuuagaag gauguuaaau caauaagguu    60
aaac                                                                 64
```

COMPOSITIONS AND METHODS RELATED TO A TYPE-II CRISPR-CAS SYSTEM IN *LACTOBACILLUS BUCHNERI*

STATEMENT OF PRIORITY

This application is a divisional application of U.S. patent application No. 15/032,985, filed on Apr. 28, 2016, which is a 35 U.S.C. § 371 national phase application of International Application Serial No. PCT/US2014/062801, filed Oct. 29, 2014, which claims the benefit, under 35 U.S.C. § 119 (e), of U.S. Provisional Application No. 61/897,670; filed Oct. 30, 2013, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-844WO_ST25.txt, 23,459 bytes in size, generated on November, 2019 and filed via EFS-Web, is provided in lieu of a paper copy. This Sequence Listing is hereby incorporated by reference into the specification for its disclosures.

FIELD OF THE INVENTION

The invention relates to a CRISPR-cas system identified in *Lactobacillus buchneri* and methods of use thereof for typing of *L. buchneri* bacterial strains, detecting the presence of a *L. buchneri* in a sample, identifying a strain of *L. buchneri* having resistance to an invasive foreign genetic element, modifying the resistance of *L. buchneri* bacteria to invasive foreign genetic elements, and for genome editing.

BACKGROUND OF THE INVENTION

Clustered Regularly Interspaced Short Palindromic Repeats (CRISPR), in combination with associated sequences (cas) constitute the CRISPR-Cas system, which confers adaptive immunity in many bacteria. CRISPR-mediated immunization occurs through the uptake of DNA from invasive genetic elements such as plasmids and phages, as novel "spacers."

Bacteria used in industrial settings for fermentation purposes are often times challenged by ubiquitous bacteriophage, occasionally interfering with manufacturing processes and product quality (Barrangou and Horvath. 2012. *Annu. Rev. Food Sci. Technol.* 3:143-162). Although phage resistance has historically relied on diversifying starter cultures and formulation based on the occurrence of phage defense systems such as restriction-modification and abortive infection (Barrangou and Horvath. 2012. *Annu. Rev. Food Sci. Technol.* 3:143-162), the recently discovered clustered regularly interspaced short palindromic repeats (CRISPR) and associated sequences (cas) have shown promise for phage resistance. CRISPR-Cas systems consist of arrays of short DNA repeats interspaced by hypervariable sequences, flanked by cas genes, that provide adaptive immunity against invasive genetic elements such as phage and plasmids, through sequence-specific targeting and interference (Barrangou et al. 2007. *Science.* 315:1709-1712; Brouns et al. 2008. *Science* 321:960-4; Horvath and Barrangou. 2010. *Science.* 327:167-70; Marraffini and Sontheimer. 2008. *Science.* 322:1843-1845; Bhaya et al. 2011. *Annu. Rev. Genet.* 45:273-297; Terns and Terns. 2011. *Curr. Opin. Microbiol.* 14:321-327; Westra et al. 2012. *Annu. Rev. Genet.* 46:311-339; Barrangou R. 2013. *RNA.* 4:267-278). Typically, invasive DNA sequences are acquired as novel "spacers" (Barrangou et al. 2007. *Science.* 315: 1709-1712), each paired with a CRISPR repeat and inserted as a novel repeat-spacer unit in the CRISPR locus. Subsequently, the repeat-spacer array is transcribed as a long pre-CRISPR RNA (pre-crRNA) (Brouns et al. 2008. *Science* 321:960-4), which is processed into small interfering CRISPR RNAs (crRNAs) that drive sequence-specific recognition. Specifically, crRNAs guide nucleases towards complementary targets for sequence-specific *nucleic acid* cleavage mediated by Cas endonucleases (Garneau et al. 2010. *Nature.* 468:67-71; Haurwitz et al. 2010. *Science.* 329:1355-1358; Sapranauskas et al. 2011. *Nucleic Acid Res.* 39:9275-9282; Jinek et al. 2012. *Science.* 337:816-821; Gasiunas et al. 2012. *Proc. Natl. Acad. Sci.* 109:E2579-E2586; Magadan et al. 2012. *PLoS One.* 7:e40913; Karvelis et al. 2013. RNA Biol. 10:841-851). These widespread systems occur in nearly half of bacteria (~46%) and the large majority of archaea (~90%). They are classified into three main CRISPR-Cas systems types (Makarova et al. 2011. *Nature Rev. Microbiol.* 9:467-477; Makarova et al. 2013. *Nucleic Acid Res.* 41:4360-4377) based on the cas gene content, organization and variation in the biochemical processes that drive crRNA biogenesis, and Cas protein complexes that mediate target recognition and cleavage.

The pickle industry relies on the use of naturally occurring bacteria for the fermentation of cucumbers in large industrial tanks (Franco et al. 2012. *Appl. Environ. Microbiol.* 78:1273-1284). To control the diverse microbiota naturally associated with pickles, and preclude spoilage by undesirable microorganisms, salting and brining are implemented in industrial settings. Unfortunately, acid- and halotolerant lactic acid bacteria often times contaminate the pickling process, resulting in a secondary fermentation, which spoils the product by generating undesirable attributes (Id.). Amongst commonly encountered bacterial contaminants, *Lactobacillus buchneri* has been repeatedly associated with spoilage of fermenting pickles (Franco et al. 2012. *Appl. Environ. Microbiol.* 78:1273-1284; Johaningsmeier et al. 2012. *J. Food Sci.* 77:M397-M404). Recent advances in genome sequencing in this species have shed light on the molecular underpinnings that allow *L. buchneri* to withstand the pickling process. In particular, determining the complete genome sequences of strains NRRL B-30929 and CD034 (Liu et al. 2011. *J. Bacteriol.* 193:4019-4020; Eikmeyer et al. 2013. *J. Bacteriol.* 167:334-343; Heinl et al. 2012. *J. Bacteriol.* 161:153-166) has established several genetic loci for substrate utilization pathways (notably lactate and carbohydrates), including the ability to convert lactic acid into acetic acid (Heinl et al. 2012. *J. Bacteriol.* 161:153-166) and 1,2-propanediol (Johaningsmeier et al. 2012. *J. Food Sci.* 77:M397-M404). Conversely, the biochemical properties of this robust bacterium have been exploited for silage inoculation to control yeast and mold growth under anaerobic conditions during the fermentation of corn, barley, wheat, and other grains into animal fodder (Heinl et al. 2012. *J. Bacteriol.* 161:153-166; Dreihuis et al. 1999. *J Appl Microbiol.* 87:583-594; Schmidt and Kung. 2010. *J. Dairy Sci.* 94:1616-1624).

Accordingly, there is a need for the development of methods for typing, identifying and detecting this important organism, *L. buchneri*, as well as for modulating the resistance of *L. buchneri* to invasive organisms, such as bacteriophage.

SUMMARY OF THE INVENTION

One aspect of the invention provides a protein-RNA complex comprising (a) a polypeptide comprising an amino acid sequence having at least 80% identity to a Cas9 of *L. buchneri* (e.g., SEQ ID NO:1); (b) a Clustered Regularly Interspaced Short Palindromic Repeats (CRISPR) RNA (crRNA) comprising a 3' region and a 5' region, wherein the 3' region comprises at least 20 consecutive nucleotides of a CRISPR repeat derived from *Lactobacillis buchneri* (e.g., SEQ ID NO:2, SEQ ID NO:3, or a fragment thereof) and the 5' region comprises at least 20 nucleotides of a spacer sequence located upstream of the repeat; and (c) a tracrRNA comprising a 5' and 3' region wherein at least a portion of the 5' region of the tracrRNA is complementary to the 3' region (CRISPR repeat sequence) of the crRNA.

A second aspect of the invention provides a chimeric RNA construct comprising (a) a crRNA comprising a 3' region and a 5' region, wherein the 3' region comprises at least 20 nucleotides of a CRISPR repeat derived from *L. buchneri* (e.g., SEQ ID NO:2, SEQ ID NO:3 or fragment thereof) and the 5' region comprises at least 20 nucleotides of a spacer sequence located immediately upstream of the repeat, and (b) a tracrRNA comprising a 5' and 3' region, wherein at least a portion of the 5' region of the tracrRNA is fully or partially complementary to the 3' region (repeat sequence) of the crRNA and the 3' region forms secondary structures.

A third aspect of the invention provides a method for site specific cleavage of a target DNA, comprising contacting a complex, a chimeric RNA or an expression cassette of this invention with the target DNA, thereby producing a site specific cleavage of the target DNA in the region defined by complementary binding of the spacer sequence of the crRNA of the complex, chimeric RNA or expression cassette to the target DNA.

A fifth aspect of the invention provides a method for cleaving a double stranded polynucleotide sequence, comprising contacting a complex, a chimeric RNA or an expression cassette of this invention with said polynucleotide, wherein the polynucleotide comprises (a) a protospacer comprising a sequence that is at least 80% complimentary to the spacer sequence in the crRNA in the complex, and (b) a protospacer adjacent motif (PAM) comprising a sequence 5'-AAAA-3' downstream from the protospacer sequence, thereby cleaving the polynucleotide in the region defined by complementary binding of the spacer sequence of the crRNA of the complex, chimeric RNA or expression cassette to the polynucleotide.

A sixth aspect of the invention comprises a method for site specific cleavage of a target DNA, comprising contacting a CRISPR RNA (crRNA) and a trans-encoded CRISPR RNA (tracrRNA) with the target DNA in the presence of a Cas9 nuclease, wherein (a) the crRNA comprises at its 3' region a repeat sequence derived from *Lactobacillus buchneri* and at its 5' region a spacer sequence derived from the target DNA, (b) the tracrRNA comprises a sequence at its 5' region that is complementary sequence to the repeat sequence of the crRNA, and (c) the spacer sequence hybridizes with a portion of the target DNA that is complementary to the spacer sequence and adjacent to a protospacer adjacent motif (PAM) comprising the nucleotide sequence 5'-AAAA-3', thereby resulting in a site specific cleavage of the target DNA in the region defined by the complementary binding of the spacer sequence of the crRNA to the target DNA.

A seventh aspect of this invention comprises a method for site-specific nicking of a polynucleotide sequence, the method comprising contacting a protein-RNA complex with a double stranded target DNA, wherein the complex comprises (a) a crRNA comprising a 3' region and a 5' region, wherein the 3' region comprises at least 20 nucleotides of a CRISPR repeat derived from *L. buchneri* (SEQ ID NO:2) and the 5' region comprises at least 20 nucleotides of a spacer sequence located upstream of the repeat, and (b) a tracrRNA comprising a 5' and 3' region wherein at least a portion of the 5' region of the tracrRNA is complementary to the 3' region (repeat sequence) of the crRNA., and (c) a polypeptide comprising the amino acid sequence of Cas9 of *L. buchneri* (e.g., SEQ ID NO:1) containing a point mutation in an RuvC active site motif; and the target DNA comprises a protospacer sequence that is at least 80% complimentary to the spacer sequence in the crRNA and a protospacer adjacent motif (PAM) sequence 5'-AAAA-3' downstream from the proto-spacer sequence, wherein the polypeptide cleaves one DNA strand of the double stranded DNA at a cleavage site located 5 nucleotides upstream of the PAM sequence resulting in site-specific nicking of said polynulceotide.

An eighth method for site-specific nicking of a polynucleotide sequence, the method comprising contacting a protein-RNA complex with a double stranded target DNA, wherein the complex comprises (a) a crRNA comprising a 3' region and a 5' region, wherein the 3' region comprises at least 20 nucleotides of a CRISPR repeat derived from *L. buchneri* and the 5' region comprises at least 20 nucleotides of a spacer sequence located upstream of the repeat, and (b) a tracrRNA comprising a 5' and 3' region wherein at least a portion of the 5' region of the tracrRNA is complementary to the 3' region (repeat sequence) of the crRN., and (c) a polypeptide comprising the amino acid sequence of Cas9 of *L. buchneri* (e.g., SEQ ID NO:1) containing a point mutation in an HNH active site motif; and the target DNA comprises a protospacer sequence that is at least 80% complimentary to the spacer sequence in the crRNA and a protospacer adjacent motif (PAM) sequence 5'-AAAA-3' downstream from the proto-spacer sequence, wherein the polypeptide cleaves one DNA strand of the double stranded DNA at a cleavage site located 5 nucleotides upstream of the PAM sequence resulting in site-specific nicking.

A ninth aspect of the invention provides a method for site-specific modification of a target DNA in vivo, the method comprising generating a crRNA comprising in its 3' region a repeat sequence derived from *Lactobacillus buchneri* and in its 5' region a spacer sequence having complementarity to a site in the target DNA in which a modification is desired; complexing the crRNA with a polypeptide having at least 80% identity with a Cas9 of *L. buchneri* (e.g., SEQ ID NO:1) and a tracrRNA comprising a sequence at its 5' region that is complementary to the repeat sequence of the crRNA, to produce a protein-RNA complex and introducing the complex into at least one cell, thereby producing a site-specific modification of the target DNA molecule in a region that is determined by the complementary spacer sequence of the crRNA to the target DNA molecule.

A tenth aspect of the invention provides a method of typing a *Lactobacillus buchneri* bacterial strain in a sample, comprising amplifying a region of DNA comprising repetitive sequences that are at least 80% identical to the repetitive sequence encoded by the nucleotide sequence of SEQ ID NO:2, SEQ ID NO:3, or a fragment thereof, in said sample to produce amplified DNA; and typing the bacterial strain based on the amplified DNA.

An eleventh aspect of the invention provides a method of detecting the presence of a *Lactobacillus buchneri* in a sample comprising amplifying in said sample a region of DNA comprising repetitive sequences that are at least 80% identical to the repetitive sequence encoded by the nucleotide sequence of SEQ ID NO:2 to produce amplified DNA, and detecting the amplified DNA.

A twelfth aspect of the invention provides a method of identifying a strain of *Lactobacillus buchneri* having resistance to an invasive foreign DNA, comprising correlating the presence of a CRISPR spacer with resistance to said invasive foreign DNA (e.g., phage DNA, plasmid DNA, chromosomal DNA, transposon) in *Lactobacillus buchneri* having a CRISPR system; and detecting said CRISPR spacer in a strain of *L. buchneri*, thereby identifying said strain as comprising said CRISPR spacer and having resistance to said invasive foreign DNA.

A thirteenth aspect of the invention provides a method for modifying (conferring or increasing) resistance of a *Lactobacillus buchneri* bacteria to an invasive foreign DNA that comprises a target DNA, comprising introducing into cells of said *Lactobacillus buchneri* bacteria a heterologous nucleic acid molecule comprising a first and a second CRISPR repeat sequence derived from *L. buchneri* and a CRISPR spacer, wherein the spacer is homologous to at least a portion of the invasive foreign DNA and is located 3' of the first CRISPR repeat sequence and 5' of the second CRISPR repeat sequence to produce transformed *L. buchneri* bacterial cells, and selecting transformed *L. buchneri* bacteria cells having modified resistance to said invasive foreign DNA.

A fourteenth aspect of the invention provides amethod for modifying (conferring or increasing) resistance of a bacterium or an archaeon to an invasive foreign DNA, comprising introducing into cells of said bacterium or archeon a heterologous nucleic acid molecule comprising a first and a second CRISPR repeat sequence derived from *Lactobacillus buchneri* and a CRISPR spacer, wherein the spacer is homologous to at least a portion of the invasive foreign DNA and is located 3' of the first CRISPR repeat sequence and 5' of the second CRISPR repeat sequence to produce transformed bacterial or archeaon cells, and selecting transformed bacteria or archeaon cells having modified resistance to said invasive foreign DNA.

The invention further provides expression cassettes, vectors and cells comprising the nucleotide sequences, polypeptides, polypeptide-nucleic acid complexes and chimeric RNAs of this invention.

These and other aspects of the invention are set forth in more detail in the description of the invention below.

BRIEF DESCRIPTION OF THE DRAWINGS

FIG. 5A shows a section of the repeat-spacer array is shown (center) (SEQ ID NO:56) with the corresponding protospacer (top) (SEQ ID NO:55), including flanking sequences (+/−10 nt) comprising the PAM, and the predicted tracrRNA sequence and structure (bottom) (SEQ ID NO:57), including the complementary anti-CRISPR repeat, as well as three putative hairpins reminiscent of characterized tracrRNAs. FIG. 5B further shows the mature cRNA (center) (SEQ ID NO:58). Also shown is the protospacer (top) (SEQ ID NO:55) and tracrRNA (bottom) (SEQ ID NO:57). FIG. 5C further shows the complementary strand (top) (SEQ ID NO:59) for the protospacer (SEQ ID NO:55) and the cleavage sites for the *L. buchneri* Cas9 HNH and RuvC motifs. Also shown is the crRNA (SEQ ID NO:58) and the tracrRNA (SEQ ID NO:57).

FIG. 6A: dual RNA guides: the target dsDNA sequence is shown (double stranded sequences at the bottom) (upper, SEQ ID NO:61 and lower, SEQ ID NO:62), with the protospacer sequence and the accompanying NNAAAA PAM; (top) dual Lbu Cas9 guide RNAs: the crRNA (SEQ ID NO:64), which consists of the spacer sequence (5' portion, upper case) and CRISPR repeat sequence 3' portion, italicized upper case); and tracrRNA (bold sequences) (, which consists of the anti-repeat (5' portion complementary to the crRNA) and 3' tail (which consists of three hairpins) (SEQ ID NO:60). FIG. 6B: single RNA guide: the corresponding chimera, which mimics the native dual guide RNA sequences includes the spacer sequence, followed by a lower stem (italicized)—bulge (bold and italicized)—upper stem (plain upper case) recapitulation of an abbreviated crRNA-CRISPRrepeat:antiCRISPRrepeat-tracrRNA, followed by the nexus (bold) and two 3' hairpins (SEQ ID NO:63). Also shown is the target dsDNA sequence is shown (double stranded sequences at the bottom) (upper, SEQ ID NO:61 and lower, SEQ ID NO:62), with the protospacer sequence and the accompanying NNAAAA PAM.

DETAILED DESCRIPTION OF THE INVENTION

Figure 1:
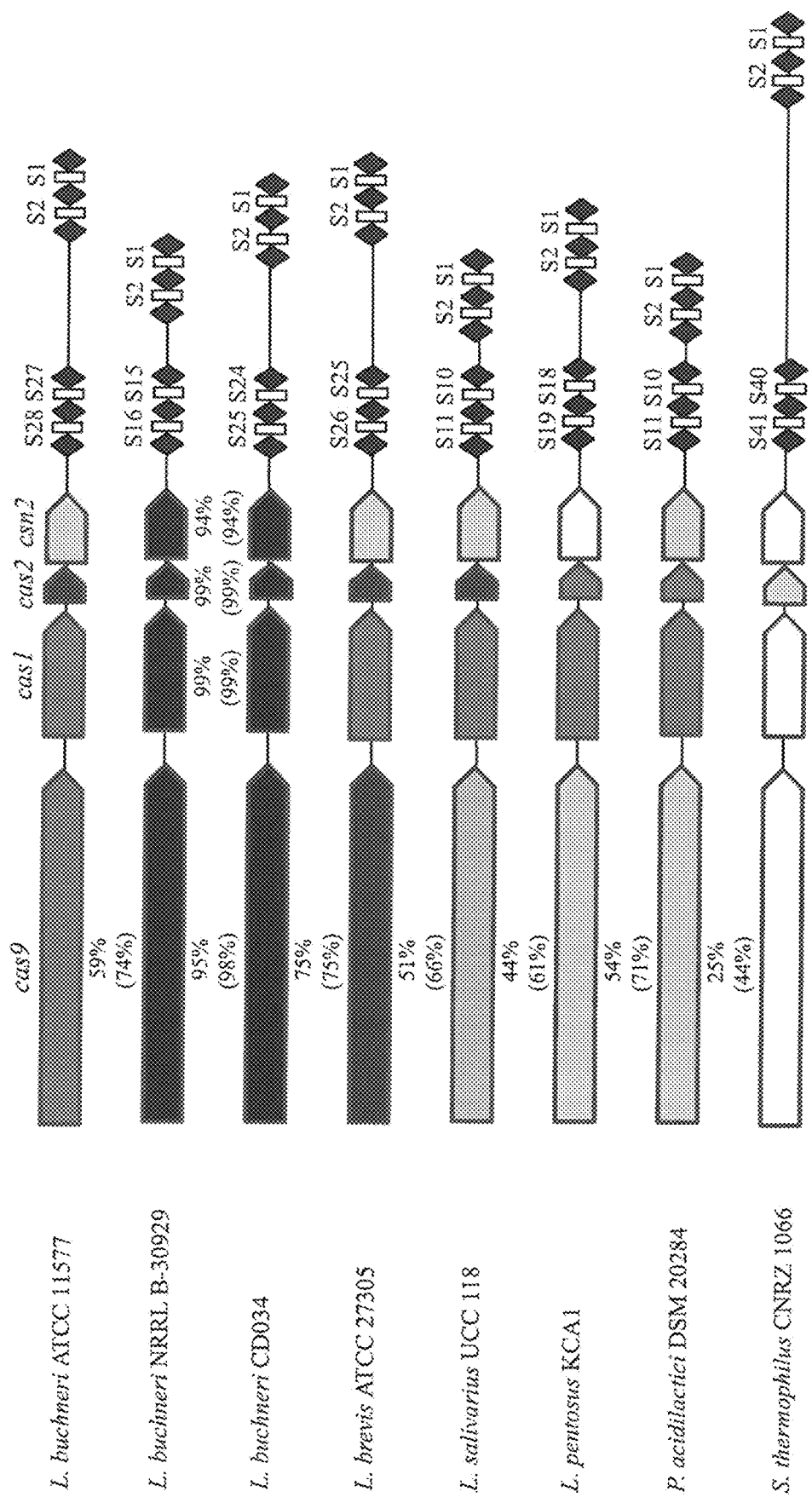
FIG. 1 shows Type II-A CRISPR-Cas systems. Left: Architecture of the Type II-A CRISPR-Cas systems in select lactic acid bacteria, containing the Type II signature cas9, together with the universal cast and cast genes as well as csn2, which is uniquely found in Type II-A systems. The gray scale reflects sequence similarity to the CD034 reference sequences, with amino acid identity (top number) and isofunctional conservation (lower number), ranging from lowest (light) to highest (dark). Right: Repeat sequences of the Type II-A CRISPR repeats in select lactic acid bacteria.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97% or more, as compared to a control. In particular embodiments, the reduction results in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The terms, "invasive foreign genetic element," "invasive foreign nucleic acid" or "invasive foreign DNA" mean DNA that is foreign to the bacteria (e.g., genetic elements from, for example, pathogens including, but not limited to, viruses, bacteriophages, and/or plasmids).

The terms "complementary" or "complementarity," as used herein, refer to the natural binding of polynucleotides under permissive salt and temperature conditions by base-pairing. For example, the sequence "A-G-T" binds to the complementary sequence "T-C-A."Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of the invention, the substantial identity exists over a region of the sequences that is at least about 16 to about 30, at least about 18 to at least about 25, at least about 18, at least about 22, at least about 25, at least about 30, at least about 40, at least about 50, about 60, about 70, about 80, about 90, about 100, about 110, about 120, about 130, about 140, about 150, or more residues in length, and any range therein. In representative embodiments, the sequences can be substantially identical over at least about 22 nucleotides. In some particular embodiments, the sequences are substantially identical over at least about 150 residues. In some embodiments, sequences of the invention can be about 70% to about 100% identical over at least about 16 nucleotides to about 25 nucleotides. In some embodiments, sequences of the invention can be about 75% to about 100% identical over at least about 16 nucleotides to about 25 nucleotides. In further embodiments, sequences of the invention can be about 80% to about 100% identical over at least about 16 nucleotides to about 25 nucleotides. In some embodiments, sequences of the invention can be about 70% identical over at least about 18 nucleotides. In other embodiments, the sequences can be about 85% identical over about 22 nucleotides. In still other embodiments, the sequences can be 100% homologous over about 16 nucleotides. In a further embodiment, the sequences are substantially identical over the entire length of the coding regions. Furthermore, in representative embodiments, substantially identical nucleotide or protein sequences perform substantially the same function.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2x (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

In particular embodiments, a further indication that two nucleotide sequences or two polypeptide sequences are substantially identical can be that the protein encoded by the first nucleic acid is immunologically cross reactive with, or specifically binds to, the protein encoded by the second nucleic acid. Thus, in some embodiments, a polypeptide can be substantially identical to a second polypeptide, for example, where the two polypeptides differ only by conservative substitutions.

Any nucleotide sequence and/or recombinant nucleic acid molecule of this invention can be codon optimized for expression in any species. Codon optimization is well known in the art and involves modification of a nucleotide sequence for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in representative embodiments of the invention, the nucleotide sequence and/or recombinant nucleic acid molecule of this invention can be codon optimized for expression in the particular species of interest. In some embodiments, the codon optimized nucleotide sequences of SEQ ID NOs:1-3 have about 70% to about 99% identity to the nucleotide sequences of SEQ ID NOs:1-3.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In any of the embodiments described herein, the nucleotide sequences and/or recombinant nucleic acid molecules of the invention can be operatively associated with a variety of promoters and other regulatory elements for expression in host cells. Thus, in representative embodiments, a recombinant nucleic acid of this invention can further comprise one or more promoters operably linked to one or more nucleotide sequences.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) Annu. Rev. Biochem. 50:349). In plants, for example, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art.

The choice of promoter will vary depending on the temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a recombinant nucleic acid molecule of the invention can be an "expression cassette" or can be comprised within an expression cassette. As used herein, "expression cassette" means a recombinant nucleic acid molecule comprising a nucleotide sequence of interest (e.g., the nucleotide sequences of the invention), wherein said nucleotide sequence is operably associated with at least a control sequence (e.g., a promoter). Thus, some embodiments of the invention provide expression cassettes designed to express the nucleotides sequences of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof).

An expression cassette of the invention also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an Agrobacterium binary vector in double or single stranded linear or circular form which may or may not be self transmissible or mobilizable. A vector as defined herein can transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast, insect, fungi, and the like). In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the nucleic acid molecules of this invention and/or expression cassettes can be comprised in vectors as described herein and as known in the art.

As used herein, "contact", contacting", "contacted," and grammatical variations thereof, refers to placing the components of a desired reaction together under conditions suitable for carrying out the desired reaction (e.g., nicking, cleavage, and/or amplifying nucleic acids). Methods and conditions for carry out nicking, cleaving, and/or amplifying reactions with nucleic acids are well-known in the art (Gasiunas et al. 2012. Proc. Natl. Acad. Sci. 109:E2579-E2586).

"Introducing," "introduce," "introduced" (and grammatical variations thereof) in the context of a polynucleotide of interest means presenting the nucleotide sequence of interest to the host organism or cell of said organism (e.g., host cell) in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different expression constructs or transformation vectors. Accordingly, these polynucleotides can be introduced into cells in a single transformation event, in separate transformation events, or, for example, they can be incorporated into an organism by conventional breeding protocols.

The term "transformation" as used herein refers to the introduction of a heterologous nucleic acid into a cell. Transformation of a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant, an animal, a mammal, an insect, and the like). Stable transformation of a cell can be detected by, for example, a Northern blot hybridization assay of RNA of the cell with nucleic acid sequences which specifically hybridize with a nucleotide sequence of a transgene introduced into a plant, animal, or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, the nucleotide sequences, constructs, expression cassettes can be expressed transiently and/or they can be stably incorporated into the genome of the host organism.

A recombinant nucleic acid molecule/polynucleotide of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid molecule/polynucleotide of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events, or, alternatively, where relevant, a nucleotide sequence can be incorporated into a plant, for example, as part of a breeding protocol.

The present invention is directed to the identification of CRISPR-Cas systems in *L. buchneri* and methods of using these genetic loci for detection and typing *L. buchneri*, as there are currently no established genotyping methods for these organisms. The invention is further directed to methods for introducing immunity to invasive foreign DNA (e.g., bacteriophage, plasmid, and the like) into bacteria using the novel CRISPR-Cas systems identified in *L. buchneri*. Finally, this invention is directed toward methods for site specific nicking, cleavage and/or modification of target DNA using the novel CRISPR-cas system described herein.

In one aspect of the invention a protein-RNA complex is provided, comprising, consisting essentially of, or consisting of (a) a polypeptide comprising, consisting essentially of, or consisting of the amino acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, and/or 100%) identity to a Cas9 of *L. buchneri* (e.g., SEQ ID NO:1, or an active fragment thereof); (b) a Clustered Regularly Interspaced Short Palindromic Repeats (CRISPR) RNA (crRNA) comprising a 3' region and a 5' region, wherein the 3' region comprises, consists essentially of, consists of at least 20 consecutive nucleotides (e.g., 20, 21, 22, 23, 24, 25, 26, 27, 28, 29, 30, 31, 32, 33, 34, 35, 36 consecutive nucleotides and the like) of a Clustered Regularly Interspaced Short Palindromic Repeats (CRISPR) repeat from *L. buchneri* (e.g., SEQ ID NO:2, or a fragment thereof) and the 5' region comprises, consists essentially of, consists of at least 20 (e.g., 20, 21, 22, 23, 24, 25, 26, 27, 28, 29, 30 and the like) nucleotides of a spacer sequence located upstream of the repeat; and (c) a tracrRNA comprising, consisting essentially of, or consisting of a 5' and 3' region wherein at least a portion (e.g., at least 7, 8, 9, 10, 11, 12, 13, 14, 15, 16, 17, 18, 19, 20, 21, 22, 23, 24, 25, 26, 27, 28, 29, 30 nucleotides, and the like) of the 5' region of the tracrRNA is complementary to the 3' region (CRISPR repeat sequence) of the crRNA. In some embodiments, a crRNA CRISPR repeat comprises, consists essentially of, consists of at least 12 consecutive nucleotides (e.g. 12, 13, 14, 15, 16, 17, 18, 19, 20, 21, 22, 23, 24, 25, 26, 27, 28, 29, 30, 31, 32, 33, 34, 35, 36 and the like) of CRISPR repeat from *L. buchneri* (e.g., SEQ ID NO:2, or a fragment thereof).

In a further aspect, the present invention provides a chimeric RNA construct comprising (a) comprising a 3' region and a 5' region, wherein the 3' region comprises, consists essentially of, consists of at least 20 consecutive nucleotides (e.g., 20, 21, 22, 23, 24, 25, 26, 27, 28, 29, 30, 31, 32, 33, 34, 35, 36 consecutive nucleotides and the like) of CRISPR repeat from *L. buchneri* (e.g., SEQ ID NO:2, or a fragment thereof) and the 5' region comprises, consists essentially of, consists of at least 20 (e.g., 20, 21, 22, 23, 24, 25, 26, 27, 28, 29, 30 and the like) nucleotides of a spacer sequence located upstream of the repeat; and (b) a tracrRNA comprising, consisting essentially of, or consisting of a 5' and 3' region wherein at least a portion (e.g., at least 7, 8, 9, 10, 11, 12, 13, 14, 15, 16, 17, 18, 19, 20, 21, 22, 23, 24, 25, 26, 27, 28, 29, 30 nucleotides, and the like) of the 5' region of the tracrRNA is complementary to the 3' region (CRISPR repeat sequence) of the crRNA and the 3' region forms secondary structures (e.g., hairpin structures). In some embodiments, a crRNA CRISPR repeat comprises, consists essentially of, consists of at least 12 consecutive nucleotides (e.g. 12, 13, 14, 15, 16, 17, 18, 19, 20, 21, 22, 23, 24, 25, 26, 27, 28, 29, 30, 31, 32, 33, 34, 35, 36 and the like) of a CRISPR repeat from *L. buchneri* (e.g., SEQ ID NO:2, or a fragment thereof).

In some embodiments, a CRISPR Cas9 polypeptide from *L. buchneri* can be SEQ ID NO:1 as set forth below.

```
                                              SEQ ID NO: 1
MKVNNYHIGLDIGTSSIGWVAIGEDGKPLRIKGKTAIGARLFQEGNPAAD

RRMFRTTRRRLSRRKWRLKLLEEIFDPYITPVDSTFFARLKQSNLSPKDS

RKEFKGSMLFPDLTDMQYHKDYPTIYHLRHALMTQDEKFDIRMVYLAIHH

IVKYRGNFLNSTPVDSFKASKVNFVDQFKKLNELYTAINPEESFQINLAN

SEDIGHQFLDPSIRKFDKKKQIPKIVPVSVDDKATDKINGKIASEIINAI

LGYKSKLDVVVQCTPVDSKSWALKFDEEDIDAKLQKILPEMDENQQSIIA

ILQNLYSQVTLNQIVPNGMSLSESMIEKYNDHHDHLKLYKKIIDQLADPK

KKAALKKAYSQYVGDDGKVIEQADFWSSVKKNLDDSDLSKQIMDLIDAEK

FMPKQRTSQNGVIPHQLHQRELDEIIEHQSKYYPWLAEINPNKHDLHLAK

YKIEELVAFRVPYYVGPMITPDDQAKSAETVFSWMERKGKEAGQITPWNF

DEKVDRNASANRFIKRMTTKDTYLIGEDVLPDESLLYEKFKVLNELNMVR

VNGKLLKVADKQAIFQDLFENYKHISVKKLQNYIKSKTGLPSDPEISGLS

DPEYFNNSLGTYNDFKKLFGNKVDEPDLQDDFEKIVEWSTVFEDKRILRE

KLNEITWLSDQQKDVLESSRYQGWGRLSKKLLTGIVNDQGERIIDELWNT

NKNFMQIQSDNDFAKRIHEANADQMKAVDVEDVLADAYTSPQNKKAIRQV

VKVVDDIQKAMGGVAPKYISIEFTRSEDRNPRRTISRQRQLENTLKDTAK

SLAKSINPELLSELDNAAKSKKGLTDRLYLYFTQLGKDIYTGKPINIDEI

STYDIDHILPQAFVKDDSLNNRVLVSKAINNGKSDNVPVQLFGAKMGHFW

KQLAEAGLISKRKLKNLQTDPDTISKYAMHGFIRRQLVETSQVIKLVANI

LGDKYRNDNTKIIEITARMNHQMRDEFGFIKNREINDYHHAFDAYLTAFL

GRYLYHRYIKLRPYFVYGDFKKFKEDKVTMRNFNFLHDLTDDTQEKIADA

ETGEVIWDRENSIQQLKDVYHYKFMLISHEVYTLRGAMFNQTVYPASDAG

KRKLIPIKADRPINVYGGYSGSADAYMAIVRIHNKKGDKYRVVGVPMRAR
```

-continued
```
DRLDAAKKVSDADCDRALKDVLTPQLTKTKKSRKTGEITQVVEDFEIVLG

KVMYRQLMIDGDKKFMLGSSTYQYNAKQLVLSDQSVKTLASKGRLDPLQE

SMDYNNVYTEILDKVNQYFSLYDMNKFRHKLNLGFSKFISFPNHNVFDGN

TKASSGKREILEEVLNGLHANPTFGNLKDIGITTPFGQLQQPNGILLSDE

AKIRYQSPTGLFERTVSLKDL
```

In some embodiments, the CRISPR Cas9 polypeptide from *L. buchneri* can be an active fragment of a CRISPER Cas9 polypeptide. Accordingly, in particular embodiments, an active fragment of a CRISPR Cas9 polypeptide from *L. buchneri* can be an active fragment of SEQ ID NO:1. In some embodiments, a *L. buchneri* Cas9 polypeptide comprises a HNH and a RuvC motif. Accordingly, an active fragment of a *L. buchneri* Cas9 polypeptide can comprise the HNH and/or RuvC nickase activities.

Figure 5A:
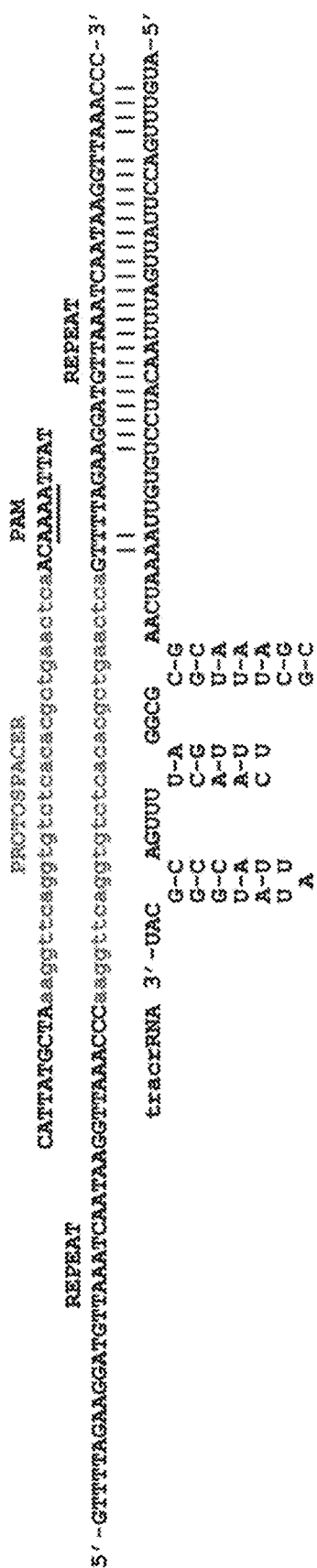
FIG. 5A-5C shows sequence and structural details for core CRISPR-Cas system elements.
Figure 5B:
Figure 5C:

In some embodiments, a crRNA of this invention, comprising a 3' region and a 5' region, can further comprise a CRISPR repeat located upstream of the spacer sequence, wherein the CRISPR repeat comprises, consists essentially, or consists of at least 12 or at least 20 consecutive nucleotides of CRISPR repeat from *L. buchneri* (e.g., SEQ ID NO:2, or a fragment thereof). Therefore, in representative embodiments, a crRNA can comprise, consist essentially of, consist of (from 5' to 3') a spacer sequence—a CRISPR repeat or a CRISPR repeat—a spacer sequence—a CRISPR repeat. As a non-limiting example see FIG. 5.

A "spacer sequence" as used herein means a sequence that is upstream (5') of a repeat sequence in a crRNA. Alternatively, when the crRNA comprises two repeat sequences (i.e., a first and a second repeat sequence) the spacer sequence is located between the two repeat sequences (i.e., the spacer sequence is located 3' of the first repeat sequence and 5' of the second repeat sequence). Generally, the spacer sequence comprises a polynucleotide sequence from a target DNA and/or an invasive foreign (e.g., heterologous) DNA (e.g., a nucleotide sequence from a bacteriophage, plasmid or chromosome that is foreign to, for example, *L. buchneri*). The spacer sequence can be at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% homologous) to the target or invasive foreign DNA. In representative embodiments, the spacer sequence is 100% homologous to the target or invasive foreign DNA. In other embodiments, the homology of the 3' region of the spacer sequence to the target or invasive foreign DNA is 100% but is less than 100% in the 5' region of the spacer. Thus, for example, the first 7, 8, 9, 10, 11, 12, 13, 14, 15, 16, and the like, nucleotides in the 3' region of a 20 nucleotide spacer sequence (seed sequence) can be 100% identical to the target or invasive foreign DNA, while the remaining nucleotides in the 5' region of the spacer sequence are at least about 70% identical to the target or invasive foreign DNA. In representative embodiments, the first 12 nucleotides of the spacer sequence can be 100% identical to the target or invasive foreign DNA, while the remaining nucleotides in the 5' region of the spacer sequence are at least about 70% identical to the target or invasive foreign DNA.

In some embodiments, a repeat sequence for use with this invention can comprise, consist essentially of, or consist of a repeat from *L. buchneri*. In some embodiments, a repeat sequence from *L. buchneri* comprises, consists essentially of, or consists of the polynucleotide sequence of SEQ ID NO:2, or a fragment thereof.

(SEQ ID NO: 2)
GTTTTAGAAGGATGTTAAATCAATAAGGTTAAACCC

In other embodiments, a repeat sequence from *L. buchneri* comprises, consists essentially of, or consists of the polynucleotide sequence of SEQ ID NO:3 (5' AUUUAACAUC-CUGUGUUAAA-3') or a fragment thereof.

The 5' region of the tracrRNA is described herein as complementary to the 3' region (repeat sequence) of the crRNA. In some embodiments, "complementary" means having about 70% or more (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) homology to the 3' repeat sequence of the crRNA. Thus, for example, the 5' region of a tracrRNA that is complementary to a 20 nucleotide sequence of a crRNA can have complementarity to about 14 out of 20 consecutive nucleotides of the crRNA repeat sequence. In representative embodiments, the 5' region of a tracrRNA that is complementary to a 20 nucleotide sequence of a crRNA can have complementarity to at least 7 consecutive nucleotides (e.g., 7, 8, 9, 10, 11, 12, 13, 14, 15, 16, 17, 18, 19, 20 nucleotides) of the crRNA repeat sequence.

In additional embodiments, the present invention provides a chimeric RNA construct comprising (a) a crRNA comprising, consisting essentially of, consisting of a 3' region and a 5' region, wherein the 3' region comprises at least 20 (e.g., 20, 21, 22, 23, 24, 25, 26, 27, 28, 29, 30, 31, 32, 33, 34, 35, 36) nucleotides of a CRISPR repeat derived from *L. buchneri* (e.g., SEQ ID NO: 2, SEQ ID NO:3, or fragments thereof) and the 5' region comprises, consists essentially of, consists of at least 20 (e.g., 20, 21, 22, 23, 24, 25, 26, 27, 28, 29, 30 and the like) nucleotides of a spacer sequence located immediately upstream of the repeat, and (b) a tracrRNA comprising a 5' and 3' region, wherein at least a portion of the 5' region of the tracrRNA is complementary to the 3' region (repeat sequence) of the crRNA and the 3' region forms secondary structures (e.g., hairpin structures).

In some embodiments, a 3' region of a crRNA of this invention can comprise, consist essentially of, consists of at least 12 (e.g., 12, 13, 14, 15, 16, 17, 18, 19, 20, 21, 22, 23, 24, 25, 26, 27, 28, 29, 30, 31, 32, 33, 34, 35, 36) nucleotides of a CRISPR repeat derived from *L. buchneri* and a 5' region of a crRNA of this invention can comprise, consist essentially of, consists of at least 12 (e.g., 12, 13, 14, 15, 16, 17, 18, 19, 20, 21, 22, 23, 24, 25, 26, 27, 28, 29, 30) nucleotides of a spacer sequence.

In particular embodiments, the 5' region of the tracrRNA of the protein-RNA complex or the chimeric RNA of this invention can comprise at least about 20 nucleotides fully or partially complementary to the at least 20 consecutive nucleotides of the 3' region of the crRNA.

The present invention further provides expression cassettes comprising nucleotide sequences, protein-RNA complexes, and/or chimeric RNAs of this invention.

The present invention additionally provides a cell comprising nucleotide sequences, protein-RNA complexes, and/or the chimeric RNAs of this invention. A cell can be from any organism useful with this invention including but not limited to a plant cell, bacteria cell, fungal cell, mammalian cell, insect cell, or archaeon cell. In particular embodiments, the cell can be from *Homo sapiens*, *Drosophila melanogaster*, *Mus musculus*, *Rattus norvegicus*, *Caenorhabditis elegans*, *Zea mays*, or *Arabidopsis thaliana*.

In a further aspect of the invention, a method for site specific cleavage of a target DNA is provided, comprising contacting a protein-RNA complex of this invention or an expression cassette a protein-RNA complex of this invention with the target DNA, thereby producing a site specific cleavage of the target DNA in the region defined by the complementary binding of the spacer sequence of the crRNA to the target nucleic acid.

In another aspect of the invention, a method for site specific cleavage of a target DNA is provided, comprising contacting a chimeric RNA of this invention, or an expression cassette comprising a chimeric RNA of this invention with the target DNA in the presence of a Cas9 nuclease, thereby producing a site specific cleavage of the target nucleic acid in a region defined by complementary binding of the spacer sequence of the crRNA to the target DNA. In some representative embodiments, the Cas9 nuclease is from *L. buchneri*.

Additional embodiments of the invention provide, a method for cleaving a double stranded polynucleotide sequence, comprising contacting a complex, a chimeric RNA or an expression cassette of this invention with said polynucleotide sequence, wherein the polynucleotide sequence comprises, consists essentially of, consists of (a) a protospacer sequence that is least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) complimentary to the spacer sequence in the crRNA in the complex, and (b) a protospacer adjacent motif (PAM) comprising, consisting essentially of, consisting of a sequence 5'-AAAA-3' downstream from the protospacer sequence, thereby cleaving the polynucleotide in the region defined by complementary binding of the spacer sequence of the crRNA of the complex, chimeric RNA or expression cassette to the polynucleotide. In some embodiments, the polypeptide of the complex cleaves both target DNA strands at a cleavage site located 5 nucleotides upstream of the PAM sequence to create blunt ends (i.e., cleaves 3nt upstream of the 3' edge of the spacer sequence, which is two nucleotides away from the PAM sequence; see, e.g., FIG. 5).

The present invention further provides a method for site specific cleavage of a target DNA, comprising contacting a CRISPR RNA (crRNA) and a trans-encoded CRISPR RNA (tracrRNA) with the target DNA in the presence of a Cas9 nuclease, wherein (a) the crRNA comprises, consists essentially of, consists of at its 3' region a repeat sequence derived from *Lactobacillus buchneri* (e.g., SEQ ID NO:2, SEQ ID NO:3, or a fragment thereof) and at its 5' region a spacer sequence derived from the target DNA, (b) the tracrRNA comprises, consists essentially of, consists of a sequence at its 5' region that is complementary sequence to the repeat sequence of the crRNA, and (c) the spacer sequence hybridizes with a portion of the target DNA that is complementary to the spacer sequence and adjacent to a protospacer adjacent motif (PAM) comprising, consisting essentially of, consisting of the nucleotide sequence 5'-AAAA-3', thereby resulting in a site specific cleavage of the target DNA in the region defined by the complementary binding of the spacer sequence of the crRNA to the target DNA. In some embodiments, the 3' region of the crRNA comprises, consists essentially of, consists of at least 20 consecutive nucleotides of the repeat sequence and the 5' region of the crRNA comprises, consists essentially of, consists of at least 20 nucleotides of the spacer sequence.

In other aspects of the invention, a method for site-specific nicking of a (+) strand of a double stranded target DNA is provided, the method comprising contacting a protein-RNA complex with a double stranded target DNA, wherein the complex comprises, consists essentially of, consists of (a) a crRNA comprising, consisting essentially of, consisting of a 3' region and a 5' region, wherein the 3' region comprises, consists essentially of, consists of at least 20 nucleotides of a CRISPR repeat derived from *L. buchneri* (SEQ ID NO:2) and the 5' region comprises, consists essentially of, consists of at least 20 nucleotides of a spacer sequence located upstream of the repeat, (b) a tracrRNA comprising a 5' and 3' region wherein at least a portion of the 5' region of the tracrRNA is complementary to the 3' region (repeat sequence) of the crRNA, and (c) a polypeptide comprising, consisting essentially of, consisting of the amino acid sequence of SEQ ID NO:1 (Cas9 of *L. buchneri*) containing a point mutation in a RuvC active site motif; and the target DNA comprises, consists essentially of, consists of a protospacer sequence that is at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) complimentary to the spacer sequence in the crRNA and a protospacer adjacent motif (PAM) sequence 5'-AAAA-3' downstream from the proto-spacer sequence, wherein the polypeptide cleaves the (+) strand of the double stranded DNA at a cleavage site located 5 nucleotides upstream of the PAM sequence, thereby producing a site-specific nick in said double stranded target DNA. Thus, by mutating the RuvC active site, the Cas9 can no longer cut the (−) strand of the target DNA (the RuvC motif cuts the (−) strand 5 nt upstream of the PAM), thereby resulting only in a cut in the (+) strand of the target DNA.

Likewise, in a further aspect of the invention, a method for site-specific nicking of the (−) strand of a double stranded target DNA is provided, the method comprising contacting a protein-RNA complex with a double stranded target DNA, wherein the complex comprises, consists essentially of, consists of (a) a crRNA comprising, consisting essentially of, consisting of a 3' region and a 5' region, wherein the 3' region comprises, consists essentially of, consists of at least 20 nucleotides of a CRISPR repeat derived from *L. buchneri* (SEQ ID NO:2; SEQ ID NO:3, or a fragment thereof) and the 5' region comprises, consists essentially of, consists of at least 20 nucleotides of a spacer sequence located a upstream of the repeat, and (b) a tracrRNA comprising, consisting essentially of, consisting of a 5' and 3' region wherein at least a portion of the 5' region of the tracrRNA is complementary to the 3' region (repeat sequence) of the crRNA., (c) a polypeptide comprising, consisting essentially of, consisting of the amino acid sequence of SEQ ID NO:1 (Cas9 of *L. buchneri*) containing a point mutation in the HNH active site motif; and the target DNA comprises, consists essentially of, consists of a protospacer sequence that is at least 80% complimentary to the spacer sequence in the crRNA and a protospacer adjacent motif (PAM) sequence 5'-AAAA-3' downstream from the proto-spacer sequence, wherein the polypeptide cleaves the (−) strand of the double stranded DNA at a cleavage site located 5 nucleotides upstream of the PAM sequence resulting in site-specific nicking of the target DNA. By providing a Cas9 having a mutation in an HNH active site, the Cas9 can no longer cut the (+) strand of the target DNA (the HNH motif cuts the (+) strand 5nt upstream of the PAM), thereby resulting only in a cut in the (+) strand of the target DNA.

A further embodiment of the invention provides a method for site-specific cleavage of a target DNA in vivo, the method comprising introducing a protein-RNA complex into at least one cell, wherein the protein-RNA complex comprises, consists essentially of, consists of a crRNA comprising in its 3' region a repeat sequence derived from *Lactobacillus buchneri* (e.g., SEQ ID NO:2, SEQ ID NO:3, or a fragment thereof) and in its 5' region a spacer sequence having complementarity to a site in the target DNA in which a modification is desired; and a polypeptide having at least 80% identity with a Cas9 of *L. buchneri* (e.g., SEQ ID NO:2, SEQ ID NO:3, or a fragment thereof) and a tracrRNA comprising, consisting essentially of, consisting of a sequence at its 5' region that is complementary to the repeat sequence of the crRNA, thereby producing a site-specific cleavage of the target DNA molecule in a region that is determined by the complementary spacer sequence of the crRNA to the target DNA molecule. In some embodiments, the target DNA contains a protospacer sequence that is least 80% complimentary to the spacer sequence in the crRNA of the protein-RNA complex, and a protospacer adjacent motif (PAM) sequence 5'-AAAA-3' downstream from the proto-spacer sequence, wherein the polypeptide cleaves both target DNA strands at the cleavage site located 5 nucleotides upstream of the PAM sequence to create blunt ends.

Once the DNA is cleaved, it can then be modified by repair mechanisms as known in the art. Thus, in some embodiments, a donor DNA can be provided for assisting in repair.

In some embodiments, the polypeptide of the protein-RNA complex can be codon optimized for the organism comprising the target DNA as described herein and as known in the art. Non-limiting examples of the types of organisms useful with this invention include plants, bacteria, fungi, mammals, insects, or archaea. In representative embodiments, the organism includes but is not limited to *Homo sapiens, Drosophila melanogaster, Mus musculus, Rattus norvegicus, Caenorhabditis elegans*, or *Arabidopsis thaliana*.

The present invention further provides a method of typing a *Lactobacillus buchneri* bacterial strain in a sample, comprising amplifying in said sample a region of DNA comprising repetitive sequences that are at least 80% identical to the nucleotide sequence encoded by SEQ ID NO:2, SEQ ID NO:3, or a fragment thereof, to produce amplified DNA; and typing the bacterial strain based on the amplified DNA.

In some embodiments, typing a bacterial strain further comprises sequencing the amplified DNA. In other embodiments, typing a bacterial strain further comprises contacting the amplified DNA with one or more restriction enzymes capable of cutting the DNA in at least one site to produce restriction fragments; determining the number and size of the restriction fragments; and typing the bacterial strain based number and size of the restriction fragments. "Determining the number and size of the restriction fragments" as used herein can mean analyzing the restriction fragments using, for example, agarose gel elextrophoresis and the like as is known in the art.

In still other embodiments, the present invention provides a method of detecting the presence of a *Lactobacillus buchneri* in a sample, comprising amplifying in said sample a region of DNA comprising repetitive sequences that are at least 80% identical to the repetitive sequence encoded by the nucleotide sequence of SEQ ID NO:2, SEQ ID NO:3, or a fragment thereof, to produce amplified DNA, and detecting the amplified DNA.

Any method of amplifying DNA known in the art and later developed can be used with this invention. A nonlimiting example of a method of amplifying includes polymerase chain reaction (PCR) as described herein and as known in the art. In some embodiments of this invention, amplifying a region of DNA comprises amplifying at least a single spacer and two repeat elements on either side of the single spacer in the repeat-spacer region of *L. buchneri*. In some embodiments of this invention, amplifying a region of DNA comprises amplifying at least about 102 consecutive nucleotides in the repeat-spacer region of *L. buchneri*.

As would be understood by those of skill in the art, when amplifying a portion of a repeat-spacer region of *L. buchneri*, any primer pair designed in conserved sequences flanking the repeat-spacer array could be used. A nonlimiting example of such primers can include 5'-CCAGAAT-GAATGATCTGTTG-3' (SEQ ID NO:10) and 5'-CATCGACGAGAACTTTG-3' (SEQ ID NO:11) (See also, the Examples).

Further embodiments of the invention provide a method of identifying a strain of *L. buchneri* having resistance to an invasive foreign DNA, comprising correlating the presence of a CRISPR spacer with resistance to said invasive foreign DNA (e.g., phage DNA, plasmid DNA, chromosomal DNA, transposon DNA) in *L. buchneri* having a CRISPR system; and detecting said CRISPR spacer in a strain of *L. buchneri*, thereby identifying said strain as comprising said CRISPR spacer and having resistance to said invasive foreign DNA.

As used herein, "correlate," "correlating" and grammatical variations thereof mean to establish or establishing an association, a relationship, or a close connection between two or more things. Thus, for example, correlating can mean establishing an association of the presence of one or more particular spacers in *L. buchneri* strains exhibiting resistance to particular invasive foreign DNA. In the context of identifying a *L. buchneri*, "correlating" means amplifying spacer sequences in a resistant strain of *L. buchneri*, sequencing the amplified spacer sequences and identifying the origin of the spacer sequence by aligning the amplified spacer sequence with protospacer sequences from invasive foreign genomes.

In representative embodiments, detecting comprises amplifying the DNA of said strain of *L. buchneri* using amplification primers for amplifying the CRISPR spacer correlated with resistance, thereby producing a CRISPR spacer amplicon when said CRISPR spacer is present; and detecting the presence or absence of said CRISPR spacer amplicon. Methods of visualizing or detecting the presence or absence of a CRSIPR spacer amplicon are well-known in the art and include, for example, gel electrophoresis.

Other aspects of the invention provide methods for modifying (e.g., conferring or increasing) resistance of a bacterium or an archaeon to an invasive foreign DNA that comprises a target DNA, comprising introducing into cells of said bacterium or an archaeon a heterologous nucleic acid molecule comprising, consisting essentially of, consisting of a first and a second CRISPR repeat sequence derived from *L. buchneri* (e.g., SEQ ID NOs:2, 3 or fragments thereof) and a CRISPR spacer, wherein the spacer is homologous to at least a portion of the invasive foreign DNA and is located 3' of the first CRISPR repeat sequence and 5' of the second CRISPR repeat sequence to produce transformed bacterial or an archaea cells, and selecting transformed bacterial or archaea cells having modified resistance to said invasive foreign DNA.

As used herein "modifying the resistance" means conferring or increasing resistance in a bacterium or an archaeon to a particular invasive foreign DNA. If the bacterium or archeaon did not have any resistance to the particular invasive foreign DNA prior to the modification, then resistance is conferred upon the bacteria to said invasive foreign DNA by introducing the heterologous nucleic acid molecule of the invention into the cells of said bacterium or archaeaon, thereby providing a level of resistance to said invasive foreign DNA that is greater than that observed to said invasive foreign DNA in a control (e.g., the control not comprising said heterologous nucleic acid molecule). However, if the bacterium or archaeon displayed some level of resistance to said invasive foreign DNA prior to the modification, by introducing the heterologous nucleic acid molecule of the invention into the cells of said bacterium or archaeon, the level of resistance to said invasive foreign DNA in said bacterium or archaeon can be increased as compared to the level of resistance to said invasive foreign DNA in a control bacterium or archaeon (e.g., a bacterium or an archaeon not comprising the heterologous nucleic acid molecule of the invention). In representative embodiments, the bacterium to which resistance to a particular invasive foreign DNA can be modified can be *Lactobacillus buchneri*.

In some embodiments, the first and second CRISPR repeat sequences of the heterologous nucleic acid molecule comprises, consists essentially of, consists of at least 20 consecutive nucleotides of a repeat sequence from *L. buchneri* and the CRISPR spacer comprises, consists essentially of, consists of at least 20 nucleotides of the invasive foreign DNA. In some embodiments, the first and second CRISPR repeat sequences comprises, consists essentially of, consists of the sequence of 5'-AUUUAACAUCCUGUGUUAAA-3' (SEQ ID NO:3). In other embodiments, the spacer sequence can be at least 80% identical to the at least a portion of the invasive foreign DNA. In still other embodiments, at least 10 nucleotides at the 3' end of the CRISPR spacer can be 100% identical to the at least a portion of the invasive foreign DNA.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Bacterial Strains, Media and Growth Conditions

*Lactobacillus buchneri* strains were obtained from the USDA-ARS Food Science Research Unit, Raleigh, N.C. (Table 1). All samples originate from an industrial manufacturing environment where cucumbers are fermented into pickles. Mixed populations of lactic acid bacteria were first grown on filter-sterilized fermented cucumber slurry (FCS), and then selected for their persistence in a diverse range of pH and salt conditions, and their ability to metabolize lactic acid. Colonies were isolated on MRA-agar plates, and subsequently identified using morphology and 16S DNA sequencing (Franco et al. 2012. *Appl. Environ. Microbiol.* 78:1273-1284; Johaningsmeier et al. 2012. *J. Food Sci.* 77:M397-M404). All strains identified at the species level as *Lactobacillus buchneri* were then used in our study. Strains originated from various sources, including commercial tank of origin and isolation time (Table 1). Isolates were designated by an identification number, suspended in glycerol, and stored at −80° C. until the start of this experiment.

Example 2. In Silico Analyses

Two complete *Lactobacillus buchneri* genome sequences, CD034 (Heinl et al. 2012. *J. Bacteriol.* 161:153-166) and NRRL B-30929 (3), and an additional draft genome, ATCC 11577, were obtained from GenBank (NC_018610, NC_015428 and NZ_ACGH01000000) at the National Center for Biotechnology Information (www.ncbi.nlm.nih.gov/) (Benson et al. 2008. *Nucleic Acids Res.* 37:D26-31). The CRISPR database CRISPRdb (Grissa et al. 2007. *BMC Bioinformatics.* 8:172) and CRISPRFinder were used to identify putative CRISPR loci in the published *L. buchneri* genomes and identify new CRISPR loci in draft genomes, respectively. After identifying several putative CRISPR loci in *L. buchneri* genomes, the basic local alignment sequence tool, BLAST (Altschul et al. 1997. *Nucleic Acids Res.* 25:3389-3402), was used to compare and contrast the sequences of cas genes, CRISPR repeats and CRISPR spacers to those of closely related systems, found in *Lactobacillus salivarius* UCC118, *Lactobacillus brevis* subsp. gravensis ATCC 27305, *Lactobacillus pentosus* KCA1, and *Pediococcus acidilactici* DSM 20284. Additionally, BLASTp analyses were used to: characterize the cas genes in *L. buchneri* (Makarova et al. 2011. *Nature Rev. Micorbiol.* 9:467-477); establish the CRISPR-Cas system type and subtype; align and determine the identity and similarity of conserved cas genes between the different bacterial species most closely related to *L. buchneri*. The putative trans-encoded CRISPR RNA (tracrRNA) sequence and structure were predicted by homology to characterized homologous sequences and predicted secondary structures (Karvelis et al. 2013. *RNA Biol.* 10:841-851; Chylinski et al. 2013. *RNA Biol.* 10:726-737). Additionally, the repeat and spacer sequences were analyzed for homology to known sequences in the GenBank database. Repeat sequences showing homology to *L. buchneri* were identified using BLASTn, non-redundant nucleotide search. Sequences showing greater than 80% similarity over the entire 36 bp repeat in the Type II-A locus and over the entire 32 bp repeat in the Type I-E loci were used for the comparative analysis of *L. buchneri*. The unique spacer sequences were compared to known foreign genetic elements such as viruses and plasmids in the following databases: non-redundant nucleotide collection (nr/nt), genomic sequence surveys (gss), high throughput genomic sequences (HTGS), and whole shotgun sequences (wgs). Spacer sequences were depicted in an overview as unique color combinations as previously described by (Horvath et al. 2008. *J. Bacteriol.* 190: 1401-1412). A proto-spacer hit was considered reliable if it showed at least 80% identity over the entire spacer sequence. Once a reliable proto-spacer was determined, the flanking sequences (~10 nt) on both sides were subjected to a comparative analysis as to determine whether conserved nucleotides derived from a proto-spacer associated motif (PAM) were present (Horvath et al. 2008. *J. Bacteriol.* 190: 1401-1412; Deveau et al. 2008. *J. Bacteriol.* 190:1390-1400, Mojica et al. 2009. *Microbiology.* 155:733-740). WebLogo (Crooks et al. 2004. *Genome Res.* 14:1188-1190) was used to generate a frequency table allowing the identification of a novel PAM.

Example 3. DNA Sequencing of *L. buchneri* CRISPR-Cas Systems

To prepare for DNA extraction, cells were propagated overnight, re-suspended in 10 mL of MRS broth and grown at 37° C. in a Coy Laboratories (Grasss Lake, Mich.) anaerobic chamber. After 48 hours, the DNA was extracted using Zymo® Fungal/Bacterial DNA Purification Kit following the special protocol for Gram-positive bacteria. PCR screening for CRISPR repeats was used to determine which CRISPR-Cas system was present in the isolated strains. To screen for the Type II-A repeat found in *L. buchneri* ATCC 1577, the primers 11577F (5'-GCTTTAGTAGTT-CAAAAC-3') (SEQ ID NO:4) and 11577R (5'-CATCAT-TGTTTTGAACTACTAC-3') (SEQ ID NO:5) were used. To screen for the Type II-A repeat found in *L. buchneri* CD034 and NRRL B-30929, the primers CD034F (5'-GGGTT-TAACCTTATTGATTTAAC-3') (SEQ ID NO:6) and CD035R (5'-GAAGGATGTTAAATCAATAAGG-3') (SEQ ID NO:7) were used. PCR amplification of the cas9 gene was performed using the primer set Cas9.1 (5'-CCTTCA-GACTGACGGTTC-3') (SEQ ID NO:8) and Cas9.Rev (5'-GTCTCGATATTGGGACCTC-3') (SEQ ID NO:9). PCR amplification of the repeat-spacer array in the 26 strains was performed using the primer set RSA.Fwd (5'-CCAGAAT-GAATGATCTGTTG-3') (SEQ ID NO:10) and RSA.Rev (5'-CATCGACGAGAACTTTG-3') (SEQ ID NO:11). PCR products were purified using Zymo® Research DNA Clean and Concentrator-5 Kit and were sent for Sanger sequencing at Eton Biolabs, Raleigh, N.C. The previously described in silico analyses were used to visualize the newly obtained repeat-spacer array sequences.

Example 4. Identification and Characterization of CRISPR-Cas Systems in *L. buchneri* Genomes Multiple putative CRISPR arrays were identified in the *L. buchneri* complete and draft genomes. Specifically, a Type I-E CRISPR-Cas system was identified in the CD034 and ATCC 11577 genomes, while a Type II-A CRISPR-Cas system was identified in the CD034, NRRL B-30929 and ATCC 11577 genomes. The Type I-E locus was defined by a highly conserved 28 nt CRISPR repeat sequence nearly identical to systems also present in multiple *Lactobacillus brevis* genomes (Table 3), with variety in the number of spacers across these loci. As anticipated, this CRISPR-Cas system includes the universal cas1 and cas2, together with the Type I cas3 signature gene (Makarova et al. 2011. *Nature Rev. Micorbiol.* 9:467-477), and the previously characterized Cascade and cash. Noteworthy, this system is not ubiquitous in *L. buchneri* genomes, limiting its potential as a universal target for typing purposes within this species (Liu et al. 2011. *Bacteriol.* 193:4019-4020; Barrangou and Horvath. 2012. *Annu. Rev. Food Sci. Technol.* 3:143-162).

Type II-A CRISPR-Cas systems were identified in all three *L. buchneri* complete and draft genomes. This locus was defined by a highly conserved 36 nt CRISPR repeat sequence homologous to those found in other *Lactobacillus* species, including *L. salivarius, L. brevis* and *L. pentosus* (FIG. 1). Likewise, this repeat sequence was somewhat homologous to CRISPR repeats found in more distant genera, including *Pediococcus* and *Streptococcus*, notably the *S. thermophilus* model Type II-A CRISPR-Cas system (FIG. 1). These systems encode the universal cas1 and cas2, together with the Type II signature cas9, as well as csn2 (Makarova et al. 2011. *Nature Rev. Micorbiol.* 9:467-477), which is unique to Type II-A subtypes (FIG. 1). A comparative analysis of Cas protein sequence conservation between these homologous Type II-A systems revealed high similarity between the CD034 and NRRL B-30929 strains, and relatively limited homology to the other aforementioned homologous systems, with 25% identity between the CD034 and CNRZ Cas9 protein sequences (FIG. 1). Notwithstanding CRISPR repeat sequence conservation and cas homologies, the hypervariable nature of these CRISPR loci across genera, species and strains is illustrated by the diversity observed in terms of CRISPR spacer number and sequences, with as few as 11 and up to 28 spacers within lactobacilli (FIG. 1).

Example 5. Diversity of Type II-A CRISPR Loci

Figure 2:
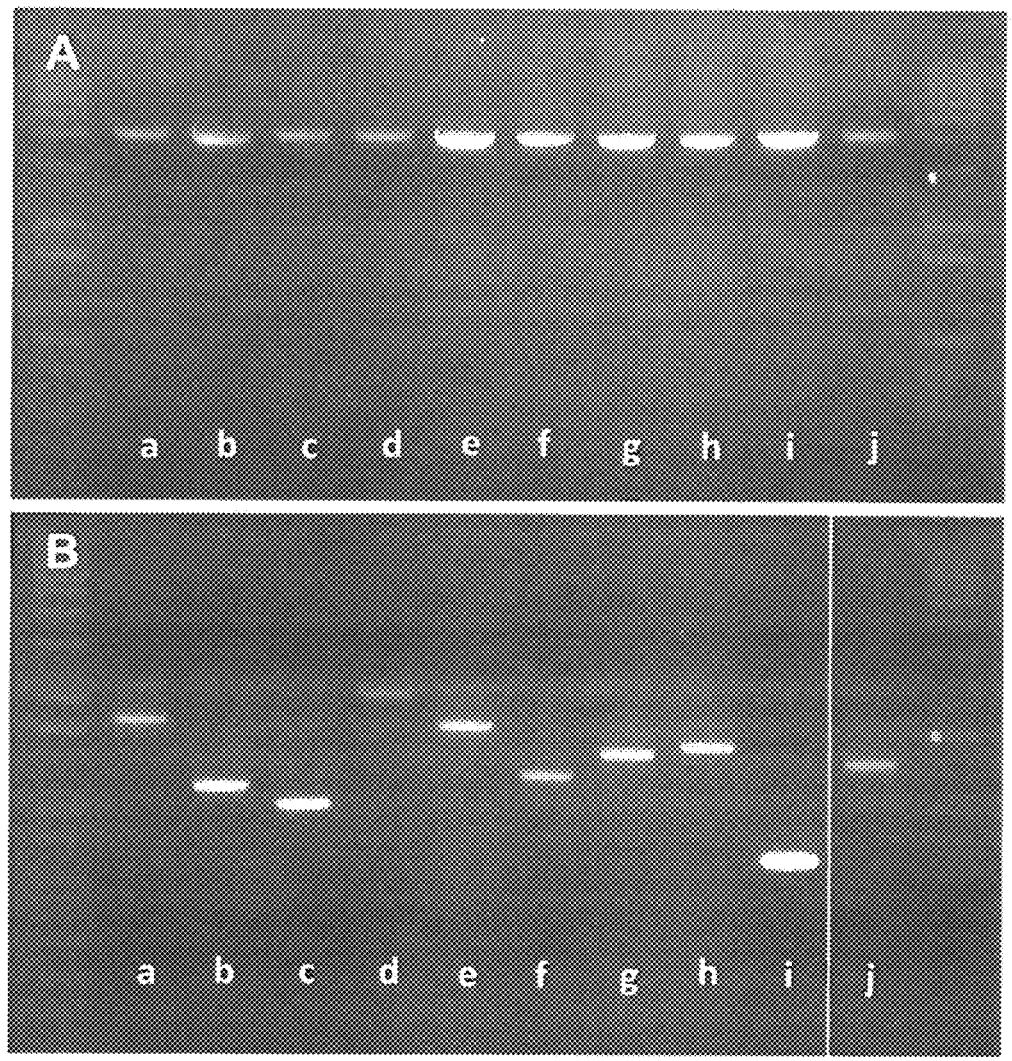
FIG. 2 shows PCR-based detection of the CRISPR-Cas elements in *L. buchneri* isolates. Top: visualization of conserved cas9 amplicons in 10 representative isolates. Bottom: visualization of the hypervariable Type II-A repeat-spacer CRISPR array in 10 diverse and representative isolates. A 1-kb DNA ladder is shown on the sides of both gels.
Figure 3:
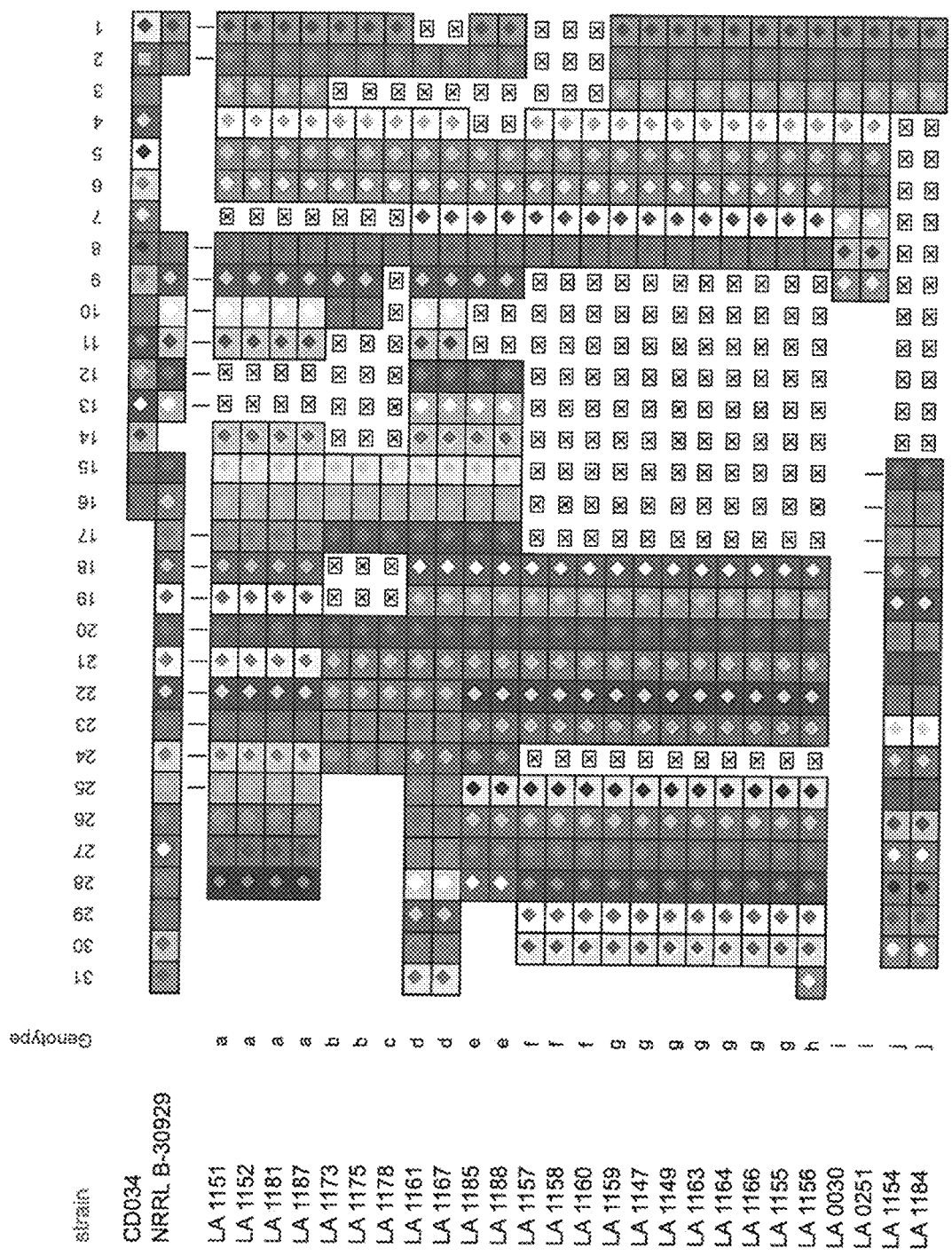
FIG. 3 shows a CRISPR spacer overview. Visualization of the Type II-A CRISPR spacer content for all 26 isolates, and comparative analysis with the loci from the two complete *L. buchneri* genomes. Only spacers are represented, all conserved repeats were removed. Each square represents a CRISPR spacer, and unique color combinations represent unique spacer sequences. Deletions/missing spacers are represented as crossed squares. Spacers are numbered in order of predicted acquisition in the locus. Each unique spacer combination was assigned a genotype (letters).

In order to determine the occurrence of Type II-A CRISPR-Cas systems in a diversity of L. buchneri strains, we carried out PCR analyses to ascertain the presence of the signature cas9 (using internal primers) and the size of the CRISPR array (using primers flanking the repeat-spacer array) in a series of industrial isolates (Table 1). Results consistently showed that this CRISPR-Cas system is ubiquitous and hypervariable in L. buchneri (FIG. 2). Indeed, we further determined the repeat-spacer variability by sequencing the PCR amplicons and reconstructing the spacer content of these strains (FIG. 3). Comparative analysis of CRISPR spacer content and sequence across 26 strains revealed ten different CRISPR genotypes containing between 9 and 29 spacers (FIG. 3). We observed conservation of ancestral CRISPR spacers revealing a common origin, including the NRRL B-30929 strain, namely spacers 1 and 2, reflecting trailer-end conservation (Chylinski et al. 2013. *RNA Biol.* 10:726-737). Furthermore, the first block of spacers (positions 1 through 8) was widely conserved throughout our strain collection. Conversely, distinct sets of consecutive spacers were shared only between certain sets of strains, revealing divergent evolutionary paths. One such set of shared consecutive spacers, can be seen in genotypes "e," "f," "g," and "h," where spacers at position 18 through 23 are strictly conserved all 13 strains across these four genotypes. This contrasts with spacers at position 17 through 25 that are only shared between genotype "a" and the NRRL B-30929 strain. The same applies to spacers at positions 15 and 16, which are shared "only" between genotypes "a" through "e". Overall, internal deletions and leader-end spacer diversity revealed hypervariability between even closely related strains. Consistent with previous reports indicating a preference for internal deletions at the trailer end (Horvath et al. 2008. *J. Bacteriol.* 190: 1401-1412; Weinberger et al. 2012. *PLoS Comput Biol.* 8:e1002475), we observed here 13 distinct spacer loss events (FIG. 3), the large majority of which (11/13) occur within the trailer half of the loci. Interestingly, LA 1156 exhibits an additional spacer at the leader end, which reflects novel spacer integration and suggests this locus is active.

Overall, the diversity found within this set of strains is interesting, considering the samples came from at least three very distinct industrial and laboratory settings.

Example 6. Origin of CRISPR Spacers and Locus Activity

In order to determine the likely origin of the CRISPR spacers, we investigated their homology to known sequences. Upon searching for homologous sequences not associated with CRISPR repeat-spacer arrays, we identified several matches to foreign genetic elements such as plasmids and bacteriophages (Table 2), as anticipated (Barrangou et al. 2007. *Science.* 315:1709-1712; Garneau et al. 2010. *Nature.* 468:67-71; Paez-Espino et al. 2013. *Nat. Commun.* 4:1430). We did observe several matches to plasmids and phages associated with lactobacilli, including examples where there is perfect identity between a CRISPR spacer and a proto-spacer from an invasive nucleic acid. This, together with the aforementioned novel spacer insertion event, is consistent with the involvement of these Type II-A CRISPR-Cas systems with adaptive immunity in L. buchneri.

Figure 4:
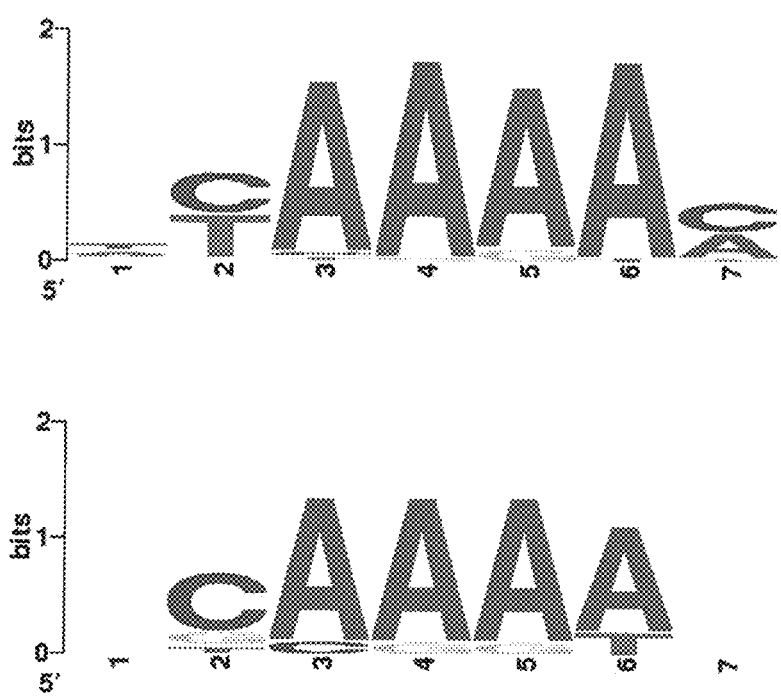
FIG. 4 shows proto-spacer adjacent motifs (PAMs). The 10 nt flanking the 3' end of the proto-spacer sequences were aligned to generate a WebLogo (Crooks et al. 2004. *Genome Res.* 14:1188-1190). Top: PAM inferred from 35 matches (proto-spacer matches showing greater than 80% similarity); bottom: PAM inferred from the top 11 matches (proto-spacer matches showing greater than 90% similarity) listed in Table 2.

Several studies have established that Cas9-mediated sequence-specific cleavage of target nucleic acid relies on the presence of a proto-spacer adjacent motif (Sapranauskas et al. 2011. *Nucleic Acid Res.* 39:9275-9282; Gasiunas et al. 2012. *Proc. Natl. Acad. Sci.* 109:E2579-E2586; Karvelis et al. 2013. *RNA Biol.* 10:841-851). This motif is also implicated in novel spacer acquisition (49). Thus, we aligned the sequences flanking the proto-spacers that showed homology to CRISPR spacer sequences and consistently observed the presence of a 5'-AAAA-3' PAM two nucleotides downstream of the proto-spacer (FIG. 4). Aligning the flanking sequences of the 35 hits revealed a 5'-AAAA-3' tetranucleotide 2 nt downstream of the proto-spacer, which was confirmed when looking at the top 11 matches (Table 2; FIG. 4). This PAM sequence is homologous to the 5'-AGAA-3' PAM previously established for the closely related CRISPR1-Cas Type II-A system from *S. thermophilus* (26, 49).

Because Cas9 is the core protein driving spacer-dependent target recognition and cleavage, we further analyzed the Cas9 sequence and investigated the presence of biochemically-relevant residues in L. buchneri. We first looked at the N-terminus RuvC motif and observed the presence of the conserved and important Asp residue implicated in the nicking of the positive target DNA strand, namely D31 within the IGLDIGT (SEQ ID NO:12) motif (Sapranauskas et al. 2011. *Nucleic Acid Res.* 39:9275-9282; Gasiunas et al. 2012. *Proc. Natl. Acad. Sci.* 109:E2579-E2586). Next, using the L. buchneri NRRL Cas9 protein sequence as a template (annotated as csnl, YP_004399187, in the publicly available genome sequence), we investigated the presence of conserved residues implicated in the nicking of the negative target strand, namely $H_{868}$-$X_{13}$-$N_{882}$-$X_8$-$N_{891}$ (SEQ ID NO:13) (Sapranauskas et al. 2011. *Nucleic Acid Res.* 39:9275-9282; Gasiunas et al. 2012. *Proc. Natl. Acad. Sci.* 109:E2579-E2586), and observed a pattern consistent with this exact spacing, and the conservation of these three biochemically relevant residues, namely YDIDHI (SEQ ID NO:14), NNRVL (SEQ ID NO:15) and INNG (SEQ ID NO:16).

Further in silico analyses were carried out to characterize elements of Type II-A CRISPR-Cas systems. Because the tracrRNA plays a critical role in Type II CRISPR-Cas systems crRNA biogenesis and interference (Gasiunas et al. 2012. *Proc. Natl. Acad. Sci.* 109:E2579-E2586; Deltcheva et al. 2011. *Nature* 471:602-607), which relies on partial sequence complementarity between the CRISPR repeat and the tracrRNA (Gasiunas et al. 2012 *Proc. Natl. Acad. Sci.* 109:E2579-E2586; Chylinski et al. 2013. *RNA Biol.* 10:726-737), we investigated the presence of a tracrRNA in the vicinity of the repeat-spacer array. We used the CRISPR repeat sequence to look for partial matches in intergenic sequences flanking cas9, as previously described. We identified a putative 90 nt tracrRNA, which shows complementarity to the CRISPR repeat (FIG. 5), and contains three predicted hairpins at the 3' end, reminiscent of the idiosyncratic tracrRNA structure of other Type II-A systems (Karvelis et al. 2013. *RNA Biol.* 10:841-851). Consistent with previous reports (Chylinski et al. 2013. *RNA Biol.* 10:726-737), the putative L. buchneri tracrRNA is located between the cas9 and cas1 genes in both CD034 and NRRL B-30929.

Example 7

We investigated the occurrence and diversity of CRISPR-Cas immune systems in L. buchneri and characterized a Type II-A system. Specifically, we show: (i) strict conservation of the 5'- GTTTTAGAAGGATGTTAAAT-CAATAAGGTTAAACCC -3' (SEQ ID NO:2) CRISPR repeat sequence; (ii) typical cas gene content and architecture for this particular subtype, which includes the cas9 signature gene; (iii) high spacer diversity between even closely related isolates, reflecting common origin, yet extensive divergence; (iv) leader-end spacer polymorphism and matches to viral sequences consistent with phage immunity; (v) core elements necessary for functional exploitation, notably important residues within Cas9, a novel PAM and the necessary tracrRNA sequence and structure.

Comparative genome analysis of CRISPR content in *L. buchneri* genomes revealed the occasional presence of a Type I-E system, and the universal occurrence of a Type II-A system (Makarova et al. 2011. *Nature Rev. Micorbiol.* 9:467-477). The conserved Type II-A system provides an attractive single-locus target for investigating the occurrence and diversity of *L. buchneri* strains, and could be broadly useful for genotyping of this species. Many studies have established that CRISPR loci can be targeted for genotyping in multiple species, and provide insights into the phylogenetic relationships between organisms, including closely related isolates (Horvath et al. 2009. *Int. J. Food Microbiol.* 131: 62-70; Liu et al. 2011. *Appl. Environ. Microbiol.* 77:4520-4526; Liu et al. 2011. *Appl. Environ. Microbiol.* 77:1946-1956; Shariat et al. 2013. *J. Clin. Microbiol.* 51:2328-2336; Sharit Et al. 2013. *Food Microbiol.* 34:164-173; Yin et al. 2013. *Appl. Environ. Microbiol.* 79:5710-5720; Dimarzio et al. 2013. *Antimicrob Agents Chemother.* Ahead of print. PMID: 23796925). Preliminary results shown here suggest that CRISPR loci could be targeted to investigate the genotype ('g")was detected in multiple strains (LA 1147, LA 1149, LA 1155, LA 1159, LA 1163, LA 1164, LA 1166), isolated at different points in time, from geographically separate locations. Likewise, genotype "a" was detected from strains isolated from different sources (FIG. 3, Table 1). This suggests that some genotypes are naturally widespread and relatively robust. Nevertheless, we also repeatedly observed the concurrent presence of multiple genotypes within space and time, suggesting a naturally diversified population. The diverse prevalence of multiple genomes may reflect predation by bacteriophage, as previously suggested (Levin et al. 2013. *PLoS Genet.* 9:e1003312; Paez-Espino et al. 2013. *Nat. Commun.* 4:1430). Furthermore, shared ancestral spacers could provide a genetic basis to establish phylogenetic relationships between strains and/or clusters of strains. This is of particular industrial interest given the widespread use of *L. buchneri* in silage inocula. Likewise, this target could be instrumental in the detection, typing and monitoring of strains that contaminate industrial vegetable fermentations such as cucumber pickling.

In addition to its genotyping potential, given the extensive circumstantial evidence implicating Type II CRISPR-Cas immune systems in adaptive immunity against phages, this system has potential for phage defense exploitation in industrial cultures. Perhaps this novel system can be exploited to enhance phage resistance in *L. buchneri* strains used to inoculate silage, similar to what has been implemented in *S. thermophilus* starter cultures (Barrangou and Horvath. 2012. *Annu. Rev. Food Sci. Technol.* 3:143-162). Indeed, the observation of the concurrent presence of two CRISPR genotypes that share spacer content with the exception of a single novel spacer at the leader end strongly suggests that this locus has the ability to acquire novel spacers in a polarized manner, as previously shown in active CRISPR loci.

Figure 6A:
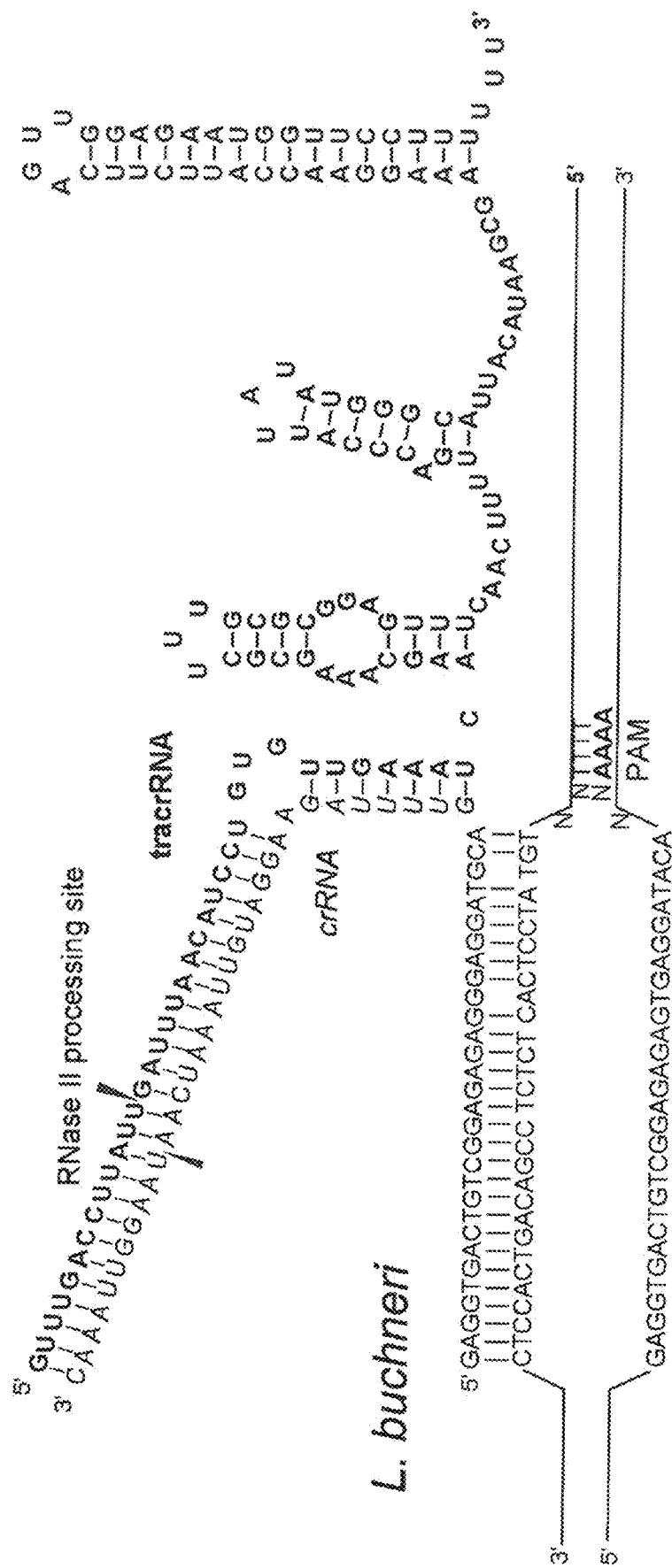
FIG. 6A-6B show *L. buchneri* (Lbu)Cas9 targeting.
Figure 6B:
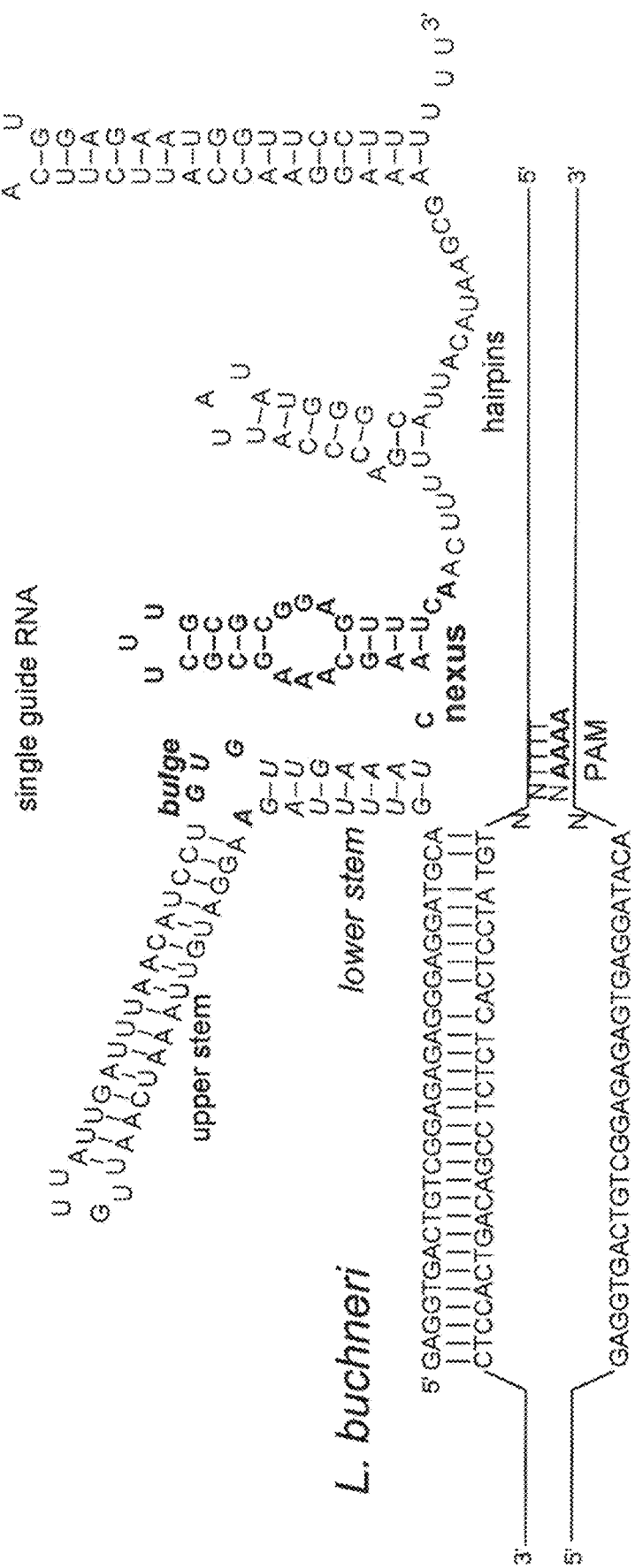

Furthermore, this Cas9, with its conserved residues, associated PAM and tracrRNA could be exploited as a novel nuclease for genome editing. Several recent studies have repeatedly established that Cas9 has tremendous potential for genome editing applications given the ability to reprogram DNA cleavage by this nimble endonuclease (Jinek et al. 2012. *Science.* 337:816-821; Cong et al. 2013. *Science.* 339:819-823; Jiang et al. 2013. *Nat. Biotechnol.* 31:233-239; Mali et al. 2013. *Science.* 339:823-826). This is readily achievable using either the native elements (Cas9, RNAse III, tracrRNA, repeat-spacer CRISPR array) or using a portable synthetic system (Cas9, chimeric guide RNA). See, for example, FIG. 6A-6B. These guides can be used to direct the LbuCas9 for sequence-specific cleavage of target dsDNA, which is then edited using DNA repair machinery, typically either NHEJ to generate random INDELs, or HDR to generate a surgical edit. However, there is a need to expand the existing Cas9 space (Chylinski et al. 2013. *RNA Biol.* 10:726-737) with novel sequences that rely on different PAMs, since the vast majority of current systems rely on the *Streptococcus pyogenes* Cas9, which is associated with a 5'-GG-3' PAM. The identification here of a novel PAM (5'-AAAA-3'), together with the accompanying putative tracrRNA, open new avenues for, for example, flexible Cas9-mediated genome editing.

TABLE 1

*Lactobacillus buchneri* strains used in this study.

| Organism | Isolate ID | 16S Accession # | CRISPR accession # | Notes |
|---|---|---|---|---|
| Lactobacillus buchneri | LA1147 | JQ249035 | KF624608 | Reduced NaCl (2%) spontaneous fermented cucumber spoilage, day 7[a] |
| Lactobacillus buchneri | LA1173 | JQ249034 | KF624603 | Reduced NaCl (2%) spontaneous fermented cucumber spoilage, day 7[a] |
| Lactobacillus buchneri | LA1175 | JQ249037 | KF624603 | Reduced NaCl (2%) spontaneous fermented cucumber spoilage, day 7[a] |
| Lactobacillus buchneri | LA1178 | JQ249040 | KF624604 | Reduced NaCl (2%) spontaneous fermented cucumber spoilage, day 7[a] |
| Lactobacillus buchneri | LA1181 | JQ249043 | KF624602 | Reduced NaCl (2%) spontaneous fermented cucumber spoilage, day 7[a] |
| Lactobacillus buchneri | LA1184 | JQ249046 | KF624611 | Reduced NaCl (2%) spontaneous fermented cucumber spoilage, day 7[a] |
| Lactobacillus buchneri | LA1151 | JQ249047 | KF624602 | Anaerobic spoilage in FCS with 4% NaCl, pH 3.8 source, day 4-6[a] |
| Lactobacillus buchneri | LA1152 | JQ249048 | KF624602 | Anaerobic spoilage in FCS with 4% NaCl, pH 3.8 source, day 4-6[a] |
| Lactobacillus buchneri | LA1154 | JQ249052 | KF624611 | Anaerobic spoilage in FCS with 4% NaCl, pH 3.8 source, day 4-6[a] |
| Lactobacillus buchneri | LA1155 | JQ249053 | KF624608 | Anaerobic spoilage in FCS with 4% NaCl, pH 3.8 source, day 4-6[a] |

TABLE 1-continued

Lactobacillus buchneri strains used in this study.

| Organism | Isolate ID | 16S Accession # | CRISPR accession # | Notes |
|---|---|---|---|---|
| Lactobacillus buchneri | LA1156 | JQ249054 | KF624609 | Anaerobic spoilage in FCS with 4% NaCl, pH 3.8 source, day 4-6[a] |
| Lactobacillus buchneri | LA1157 | JQ249055 | KF624607 | Anaerobic spoilage in FCS with 4% NaCl, pH 3.8 source, day 4-6[a] |
| Lactobacillus buchneri | LA1158 | JQ249056 | KF624607 | Anaerobic spoilage in FCS with 4% NaCl, pH 3.8 source, day 4-6[a] |
| Lactobacillus buchneri | LA1159 | JQ249057 | KF624608 | Anaerobic spoilage in FCS with 4% NaCl, pH 3.8 source, day 4-6[a] |
| Lactobacillus buchneri | LA1160 | JQ249058 | KF624607 | Anaerobic spoilage in FCS with 4% NaCl, pH 3.8 source, day 4-6[a] |
| Lactobacillus buchneri | LA1161 | JQ249060 | KF624605 | Commercial anaerobic spoilage with 4% NaCl, pH 3.8 FCS source, day 4-6[a] |
| Lactobacillus buchneri | LA1163 | JQ249062 | KF624608 | Commercial anaerobic spoilage with 4% NaCl, pH 3.8 FCS source, day 4-6[a] |
| Lactobacillus buchneri | LA1164 | JQ249063 | KF624608 | Commercial anaerobic spoilage with 4% NaCl, pH 3.8 FCS source, day 4-6[a] |
| Lactobacillus buchneri | LA1166 | JQ249064 | KF624608 | Commercial anaerobic spoilage with 4% NaCl, pH 3.8 FCS source, day 4-6[a] |
| Lactobacillus buchneri | LA1167 | JQ249065 | KF624605 | Commercial anaerobic spoilage with 4% NaCl, pH 3.8 FCS source, day 4-6[a] |
| Lactobacillus buchneri | LA1149 | JQ086334 | KF624608 | Commercial cucumber fermentation spoilage isolate in 2010[b] |
| Lactobacillus buchneri | LA1185 | N/A | KF624606 | Unpublished, isolate from Johanningsmeier 2012 study[c] |
| Lactobacillus buchneri | LA1187 | N/A | KF624602 | Unpublished, isolate from Johanningsmeier 2012 study[c] |
| Lactobacillus buchneri | LA1188 | N/A | KF624606 | Unpublished, isolate from Johanningsmeier 2012 study[c] |
| Lactobacillus buchneri | LA0030 | N/A | KF624610 | Unpublished, isolate from Johanningsmeier 2012 study[c] |
| Lactobacillus buchneri | LA0251 | N/A | KF624610 | Unpublished, isolate from Johanningsmeier 2012 study[c] |

[a]Johanningsmeier et al. 2012. *J. Food Sci.* 77: M397-M404,
[b]Franco et al. 2012, *Appl. Environ. Microbiol.* 78: 1273-1284 and
[c]unpublished data.

TABLE 2

L. buchneri CRISPR spacer matches

| Strain | Spacer No. | Left Flank | Proto-Spacer Sequence | Right Flank | Match (N/30) | Proto-spacer match | Annotation |
|---|---|---|---|---|---|---|---|
| LA 1175 | 15 | aaaattcaga | CAACAAAAAAGCGCgcaaa TCCGCAACGGCCATTacgct | | 30 | Food metagenome ASXE01000335 | Putative phage Mu Gam protein |
| LA 1154 | 12 | atgaagttca | AGCTGTGTCAAACTAacaaa CGTTGAATCCCAAGGactta | | 29 | Food metagenome ASXE01000117 | Putative phage transcriptional activator |
| LA 1152 | 2 | ctggttttat | AAACGGATATTGCGGtgaaa CTTATATTAACGAGCtggtt | | 30 | Lactobacillus brevis pLB925A02 | Plasmid mobilization protein |
| LA 1152 | 2 | ctggttttat | AAACGGATATTGCGGtgaaa CTTATATTAACGAGCtggtt | | 30 | Lactobacillus buchneri CD034 pCD034-1 | Mobilization protein |
| LA 1147 | 10 | agaatatcga | CAACGCAGCTAAAGAccaga TAATCGTCAGAATTAaatta | | 29 | Food metagenome ASXE01000848 | Putative phage nucleotide-binding protein |
| NRRL B-30929 | 9 | taagcttggt | GGAAAAAGGTGGCGGtcaag CCGCTTTGTGCAAGGaaatg | | 30 | Lactobacillus kefiranofaciens ZW3 pWW2 | Conjugal transfer protein |
| NRRL B-30929 | 3 | ttacgcttta | ACCGAGTTTCGTGATgcaaa CTCAAAAGTAGCTACaacta | | 30 | Lactobacillus paracasei pLP5402 | Plasmid replication initiation |
| LA 1188 | 1 | ttcttagatg | CCGCTTACTTGCCGTttcaa TAAAGCGGGATATCGaaaga | | 28 | Lactobacillus plantarum ZJ316 pLP-ZJ103 | Transposase |

TABLE 2 -continued

L. buchneri CRISPR spacer matches

| Strain | Spacer No. | Left Flank | Proto-Spacer Sequence | Right Flank | Match (N/30) | Proto-spacer match | Annotation |
|---|---|---|---|---|---|---|---|
| LA 1161 | 21 | aaaattcaga | CAACAAAAAAAGCGCgcaaa TCCGCAACGGCCATTacgct | | 30 | Food metagenome ASXE01000848 | Putative phage nucleotide-binding protein |
| LA 1161 | 23 | cattatgcta | AAGGTTCAGGTGTCTacaaa CACACGCTGAACTAGattat | | 29 | Lactobacillus kisonensis F0435 | Phage tail tape measure protein |
| LA 1161 | 24 | ctttatctag | GAAATAAGCAGCCTCccaaa ATTTGAAGCACCATGaatga | | 30 | Food metagenome ASXE01000470 | Putative phage lyzozyme |

TABLE 3

Type I-E CRISPR-Cas sytems in L. buchneri genomes and closely related lactobacilli

| Genus | Species | Strain | CRISPR Repeat | No. of Spacers |
|---|---|---|---|---|
| Lactobacillus | buchneri | CD 034 | GTATTCCCCACGTA CGTAGGGGTGATCC | 48 |
| Lactobacillus | buchneri | CD 034 | GTATTCCCCACGTG TGTAGGGGTGATCC | 3 |
| Lactobacillus | buchneri | ATCC 11577 | GTATTCCCCATGTA TGTGGGGGTGATCC | 3 |
| Lactobacillus | brevis | KB 290 | GTATTCCCCACACA TGTGGGGGTGATCC | 28 |
| Lactobacillus | brevis | ATCC 367 | GTATTCCCCACACA TGTGGGGGTGATCC | 29 |
| Lactobacillus | brevis | ATCC 367 | GTATTCCCCACAGG TGTGGGGGTGATCC | 28 |

That which is claimed is:

1. A chimeric RNA construct comprising:
   (a) a crRNA comprising a 3' region and a 5' region, wherein the 3' region comprises at least 20 consecutive nucleotides of a Clustered Regularly Interspaced Short Palindromic Repeats (CRISPR) repeat derived from *L. buchneri* and the 5' region comprises at least 20 consecutive nucleotides of a spacer sequence located immediately upstream of the repeat, and
   (b) a tracrRNA derived from *L. buchneri* comprising a 5' and 3' region, wherein at least a portion of the 5' region of the tracrRNA is complementary to the 3' region (repeat sequence) of the crRNA and the 3' region forms secondary structures with the target DNA in the presence of a Cas9 nuclease, and wherein the tracrRNA comprises a nucleotide sequence having at least 90% sequence identity to:
   (i) the nucleotide sequence of SEQ ID NO:60, or
   (ii) the nucleotide sequence comprising consecutive nucleotides 11-137 of SEQ ID NO:60.

2. The chimeric RNA construct of claim 1, wherein the CRISPR repeat is the sequence of 5'-AUUUAACAUCCU-GUGUUAAA-3' (SEQ ID NO:3).

3. The chimeric RNA construct of claim 1, wherein the CRISPR repeat is an RNA encoded by the nucleotide sequence of SEQ ID NO:2.

4. An expression cassette comprising the chimeric RNA construct of claim 1.

5. A vector comprising the expression cassette of claim 4.

6. A cell comprising the chimeric RNA construct of claim 1, optionally wherein the cell is a plant cell, bacterial cell, fungal cell, mammalian cell, insect cell, or archaeon cell.

7. A chimeric RNA-protein complex comprising:
(a) a crRNA comprising a 3' region and a 5' region, wherein the 3' region comprises at least 20 consecutive nucleotides of a Clustered Regularly Interspaced Short Palindromic Repeats (CRISPR) repeat derived from *L. buchneri* and the 5' region comprises at least 20 consecutive nucleotides of a spacer sequence located immediately upstream of the repeat, and
(b) a tracrRNA derived from *L. buchneri* comprising a 5' and 3' region, wherein at least a portion of the 5' region of the tracrRNA is complementary to the 3' region (repeat sequence) of the crRNA and the 3' region forms secondary structures with the target DNA in the presence of a Cas9 nuclease, and wherein the tracrRNA comprises a nucleotide sequence having at least 90% sequence identity to:
(i) the nucleotide sequence of SEQ ID NO:60, or
(ii) the nucleotide sequence comprising consecutive nucleotides 11-137 of SEQ ID NO:60; and
(c) a polypeptide comprising an amino acid sequence having at least 80% sequence identity to the Cas9 polypeptide from *L. buchneri* comprising SEQ ID NO:1.

8. The chimeric RNA-protein complex of claim 7, wherein the CRISPR repeat is the sequence of 5'-AUUUAA-CAUCCUGUGUUAAA-3' (SEQ ID NO:3).

9. The chimeric RNA-protein complex of claim 7, wherein the CRISPR repeat is an RNA encoded by the nucleotide sequence of SEQ ID NO:2.

10. The chimeric RNA-protein complex of claim 7, wherein the Cas9 polypeptide comprises an HNH motif and a RuvC motif.

11. The chimeric RNA-protein complex of claim 10, wherein the HNH motif and/or the RuvC motif comprise a point mutation.

12. An expression cassette comprising the chimeric RNA-protein complex of claim 7.

13. A vector comprising the expression cassette of claim 12.

14. A cell comprising the chimeric RNA-protein complex of claim 7, optionally wherein the cell is a plant cell, bacterial cell, fungal cell, mammalian cell, insect cell, or archaeon cell.

15. A method for cleaving a double stranded polynucleotide sequence, comprising contacting the chimeric RNA-protein complex of claim 7 with the double stranded polynucleotide sequence, wherein the double stranded polynucleotide comprises
(a) a protospacer sequence comprising a sequence that is least 80% complimentary to the spacer sequence in the crRNA in said complex, and
(b) a protospacer adjacent motif (PAM) comprising a sequence 5'-AAAA-3' downstream from the proto-spacer sequence.

16. The method of claim 15, wherein the polypeptide of the complex cleaves both strands of the polynucleotide at a cleavage site located 5 nucleotides upstream of the PAM sequence to create blunt ends.

17. The method of claim 15, wherein the nucleotide sequence is codon optimized for an organism comprising the target DNA.

18. The method of claim 17, wherein the organism is a plant, bacteria, fungus, mammal, insect, or archaeon.

19. A method for site-specific nicking of a (+) strand of a double stranded target DNA, comprising contacting the double stranded target DNA with the chimeric RNA-protein-complex of claim 7, wherein the polypeptide of the chimeric RNA-protein complex comprises a point mutation in an RuvC active site motif; and the target DNA comprises a protospacer sequence that is at least 80% complimentary to the spacer sequence in the crRNA and a protospacer adjacent motif (PAM) sequence 5'-AAAA-3' downstream from the proto-spacer sequence, wherein the polypeptide cleaves the (+) strand of the double stranded DNA at a cleavage site located 5 nucleotides upstream of the PAM sequence, thereby producing a site-specific nick in said double stranded target DNA.

20. A method for site-specific nicking of the (−) strand of a double stranded target DNA, comprising contacting the double stranded target DNA with the chimeric RNA-protein-complex of claim 7, wherein the polypeptide of the chimeric RNA-protein-complex comprises a point mutation in an HNH active site motif; and the target DNA comprises a protospacer sequence that is at least 80% complimentary to the spacer sequence in the crRNA and a protospacer adjacent motif (PAM) sequence 5'-AAAA-3' downstream from the proto-spacer sequence, wherein the polypeptide cleaves the (−) strand of the double stranded DNA at a cleavage site located 5 nucleotides upstream of the PAM sequence resulting in site-specific nicking of the target DNA.

21. The chimeric RNA-protein complex of claim 7, wherein the Cas9 polypeptide from *L. buchneri* comprises the amino acid sequence of SEQ ID NO:1.

* * * * *

UNITED STATES PATENT AND TRADEMARK OFFICE
CERTIFICATE OF CORRECTION

PATENT NO. : 11,499,169 B2
APPLICATION NO. : 16/774659
DATED : November 15, 2022
INVENTOR(S) : Barrangou et al.

It is certified that error appears in the above-identified patent and that said Letters Patent is hereby corrected as shown below:

On the Title Page

(56) References Cited, OTHER PUBLICATIONS, Page 2, Column 2, Cochrane et al. cite, Line 26: Please correct "(2018)" to read --(2016)--

(56) References Cited, OTHER PUBLICATIONS, Page 2, Column 2, Final Office Action cite, Line 27: Please correct "Jul. 30, 2015" to read --Jul. 30, 2018--

(56) References Cited, OTHER PUBLICATIONS, Page 3, Column 1, Gomaa et al. cite, Line 56: Please correct "5(1):000928-13" to read --5(1):e00928-13--

(56) References Cited, OTHER PUBLICATIONS, Page 3, Column 2, Makarova et al. cite, Line 12: Please correct "*Nat. Microbiol.*" to read --*Nat. Rev. Microbiol.*--

(56) References Cited, OTHER PUBLICATIONS, Page 3, Column 2, Marraffini and Sontheimer cite, Line 17: Please correct "*Science* (2005)" to read --*Science* (2008)--

(56) References Cited, OTHER PUBLICATIONS, Page 3, Column 2, Selle K, Barrangou R. cite, Line 45: Please correct "21(4)" to read --23(4)--

(56) References Cited, OTHER PUBLICATIONS, Page 4, Column 1, Chylinski et al. cite, Line 30: Please correct "familities" to read --families--

(56) References Cited, OTHER PUBLICATIONS, Page 4, Column 2, Sapranauskas et al. cite, Line 11: Please correct "system provided immunity" to read --system provides immunity--

(56) References Cited, OTHER PUBLICATIONS, Page 4, Column 2, Yin, Shuang et al. cite, Lines 23-24: Please correct "Toxic-Producint" to read --Toxic-Producing--

Signed and Sealed this
Twenty-first Day of March, 2023

Katherine Kelly Vidal
*Director of the United States Patent and Trademark Office*

CERTIFICATE OF CORRECTION (continued)
U.S. Pat. No. 11,499,169 B2

(56) References Cited, OTHER PUBLICATIONS, Page 4, Column 2, Hidalgo-Cantabrana et al. cite, Line 51: Please correct "15774-15763 (2019)" to read --15774-15783 (2019)--

(56) References Cited, OTHER PUBLICATIONS, Page 5, Column 1, Dang, Y. et al. cite, Line 12: Please correct "16(280):11-10 (2015)" to read --16(280):1-10 (2015)--

In the Specification

Column 4, Line 29: Please correct "crRN" to read --crRNA--

Column 5, Line 52: Please correct "cast and cast" to read --*cas*1 and *cas*2--

Column 27, Lines 47-48: Please correct "(-10 nt)" to read --(~10 nt)--

Column 28, Line 41: Please correct "Cascade and cash" to read --Cascade and *cas6*--

Column 28, Line 44: Please correct "Liu et al. 2011. *Bacteriol.*" to read --Liu et al. 2011., *J. Bacteriol.*--

Column 31, Line 28: Please correct "Sharit Et al." to read --Shariat et al.--